(12) United States Patent
Weber

(10) Patent No.: US 8,911,970 B2
(45) Date of Patent: Dec. 16, 2014

(54) SOYBEAN-BASED FERMENTATION MEDIA, METHODS OF MAKING AND USE

(71) Applicant: Fermalogic, Inc., Chicago, IL (US)

(72) Inventor: J. Mark Weber, Chicago, IL (US)

(73) Assignee: Fermalogic, Inc., Chicago, IL (US)

( * ) Notice: Subject to any disclaimer, the term of this patent is extended or adjusted under 35 U.S.C. 154(b) by 0 days.

(21) Appl. No.: 13/847,091

(22) Filed: Mar. 19, 2013

(65) Prior Publication Data

US 2013/0288308 A1    Oct. 31, 2013

Related U.S. Application Data

(62) Division of application No. 12/768,425, filed on Apr. 27, 2010, now Pat. No. 8,426,189.

(60) Provisional application No. 61/173,662, filed on Apr. 29, 2009.

(51) Int. Cl.
| | |
|---|---|
| *C12P 19/62* | (2006.01) |
| *C12N 1/38* | (2006.01) |
| *C12P 19/00* | (2006.01) |
| *C12P 19/60* | (2006.01) |
| *C12P 19/44* | (2006.01) |
| *C12N 1/20* | (2006.01) |

(52) U.S. Cl.
CPC .. *C12P 19/62* (2013.01); *C12N 1/38* (2013.01)
USPC .............. 435/76; 435/74; 435/75; 435/72; 435/41; 435/243; 435/252.1

(58) Field of Classification Search
None
See application file for complete search history.

(56) References Cited

U.S. PATENT DOCUMENTS

| | | | |
|---|---|---|---|
| 4,428,876 A | 1/1984 | Iwamura | |
| 5,320,949 A | 6/1994 | Shen | |
| 5,352,384 A | 10/1994 | Shen | |
| 5,637,561 A | 6/1997 | Shen et al. | |
| 5,637,562 A | 6/1997 | Shen et al. | |
| 6,090,416 A | 7/2000 | Iritani et al. | |
| 6,616,953 B2 | 9/2003 | Fidler et al. | |
| 8,426,189 B2 | 4/2013 | Weber | |
| 2008/0044861 A1 | 2/2008 | Weber | |

FOREIGN PATENT DOCUMENTS

| | | |
|---|---|---|
| CA | 2240795 C | 5/2002 |
| JP | 05176756 A | 7/1993 |

OTHER PUBLICATIONS

Hessler et al., "Isolation of Isoflavones from Soy-Based Fermentations of the Erythromycin-Producing Bacterium *Saccharopolyspora erythraea*", Applied Microbiology and Biotechnology, 1997, pp. 398-404, vol. 47, Springer-Verlag.

Minas et al., "Improved Erythromycin Production in a Genetically Engineered Industrial Strain of *Saccharopolyspora erythraea*", Biotechnology, Progress., 1998, pp. 561-566, vol. 14.

Reeves et al., "Knockout of the Erythromycin Biosynthetic Cluster Gene, eryBl, Blocks Isoflavone Glucoside Bioconversion During Erythromycin Fermentations in Aeromicrobium Erythreum but Not in *Saccharopolyspora erythraea*", Applied and Environmental Microbiology, Dec. 2008, pp. 7383-7390, vol. 74, No. 23.

Dahod, "Raw Materials Selection and Medium Development for Industrial Fermentation Processes", Manual of Industrial Microbiology and Biotechnology, Chapter 17—2nd Edition; Ed. Demain and Davies, Jan. 28, 1999, pp. 213-220, American Society for Microbiology.

*Primary Examiner* — Blaine Lankford
*Assistant Examiner* — David Berke-Schlessel
(74) *Attorney, Agent, or Firm* — Thompson Coburn LLP; Charles P. Romano

(57) ABSTRACT

Fermentation media containing an isoflavone-depleted soybean meal or isoflavone-depleted soybean meal product and at least one exogenous added ingredient that comprises a substrate for microbial growth are provided. Methods of making a fermentation medium comprising an isoflavone-depleted soybean meal or isoflavone-depleted soybean meal product and methods for obtaining a fermentation product are also provided. The present invention is further directed to fermentation broths obtained by the media and methods. The present invention is also directed to feed additives produced from fermentation broths obtained by the methods.

16 Claims, 13 Drawing Sheets

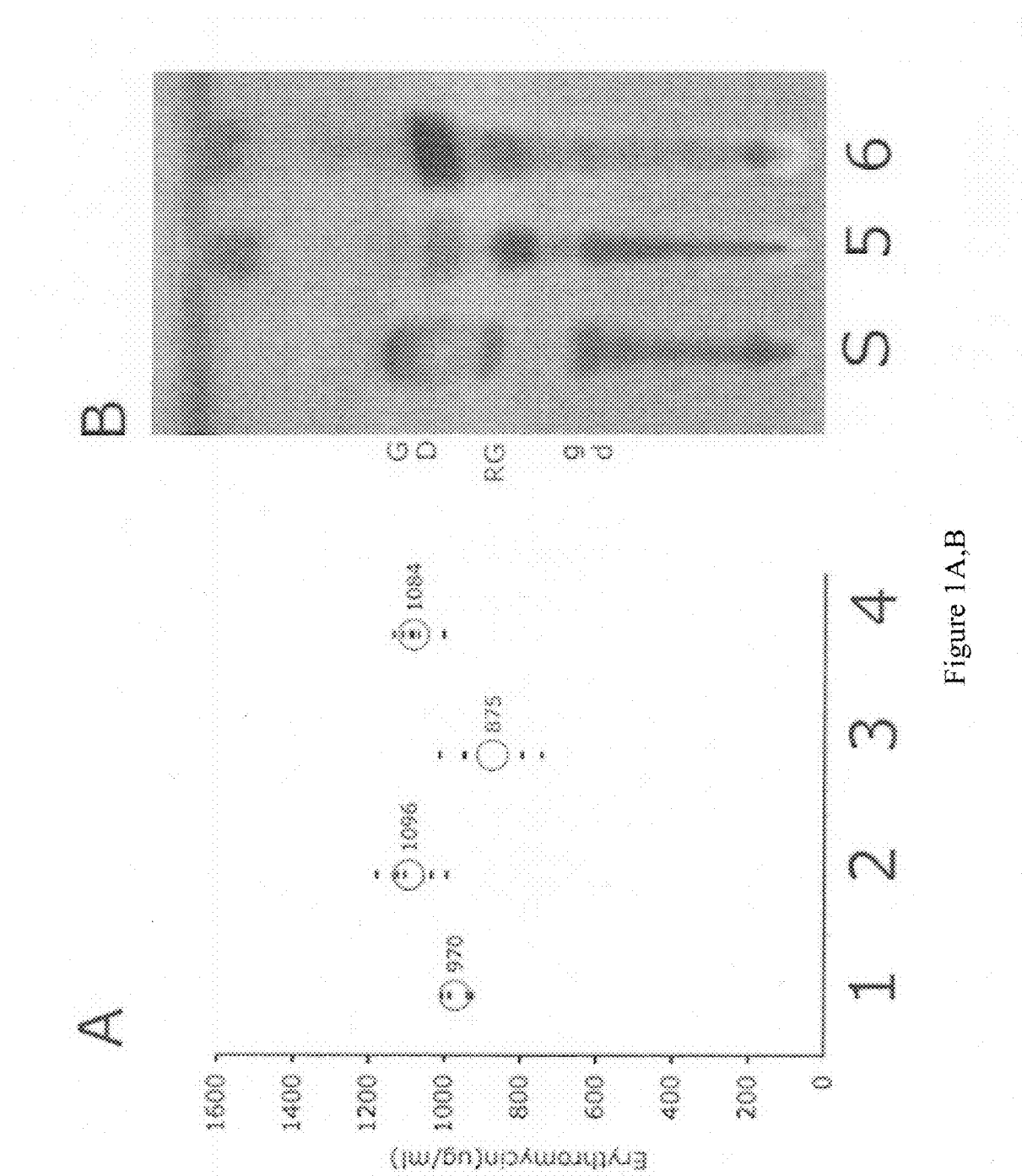
Figure 1A,B

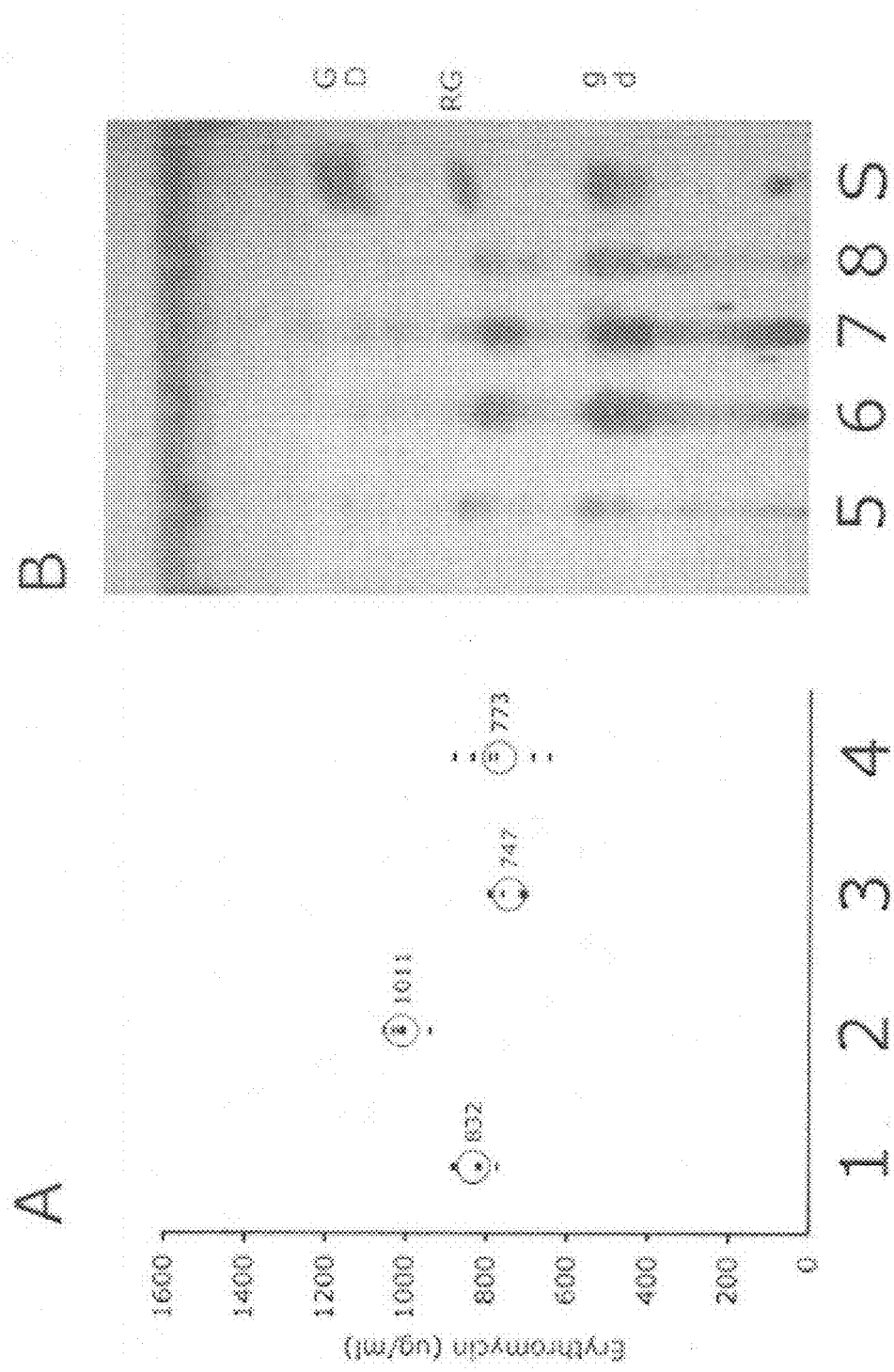
Figure 2A,B

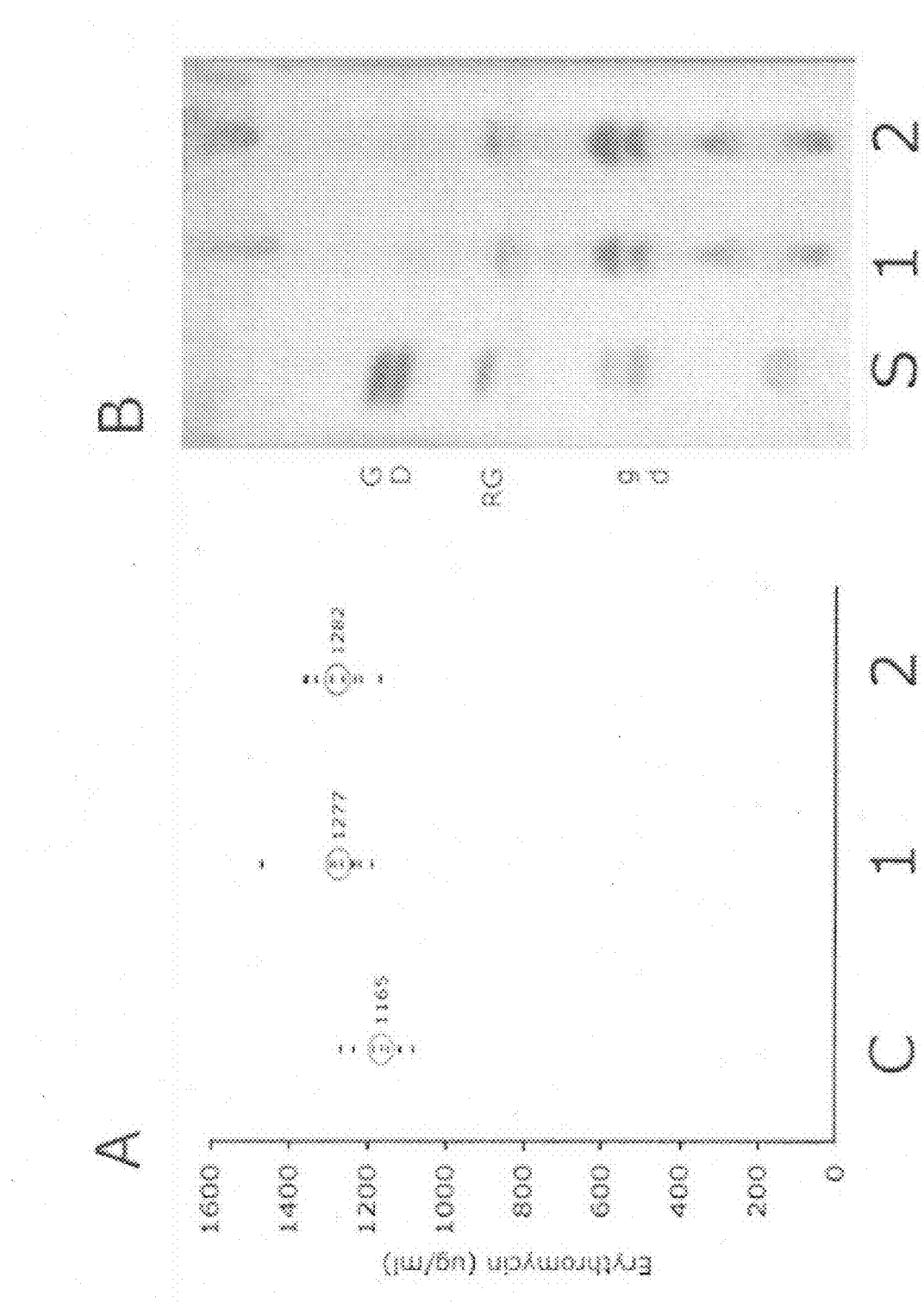
Figure 3A,B

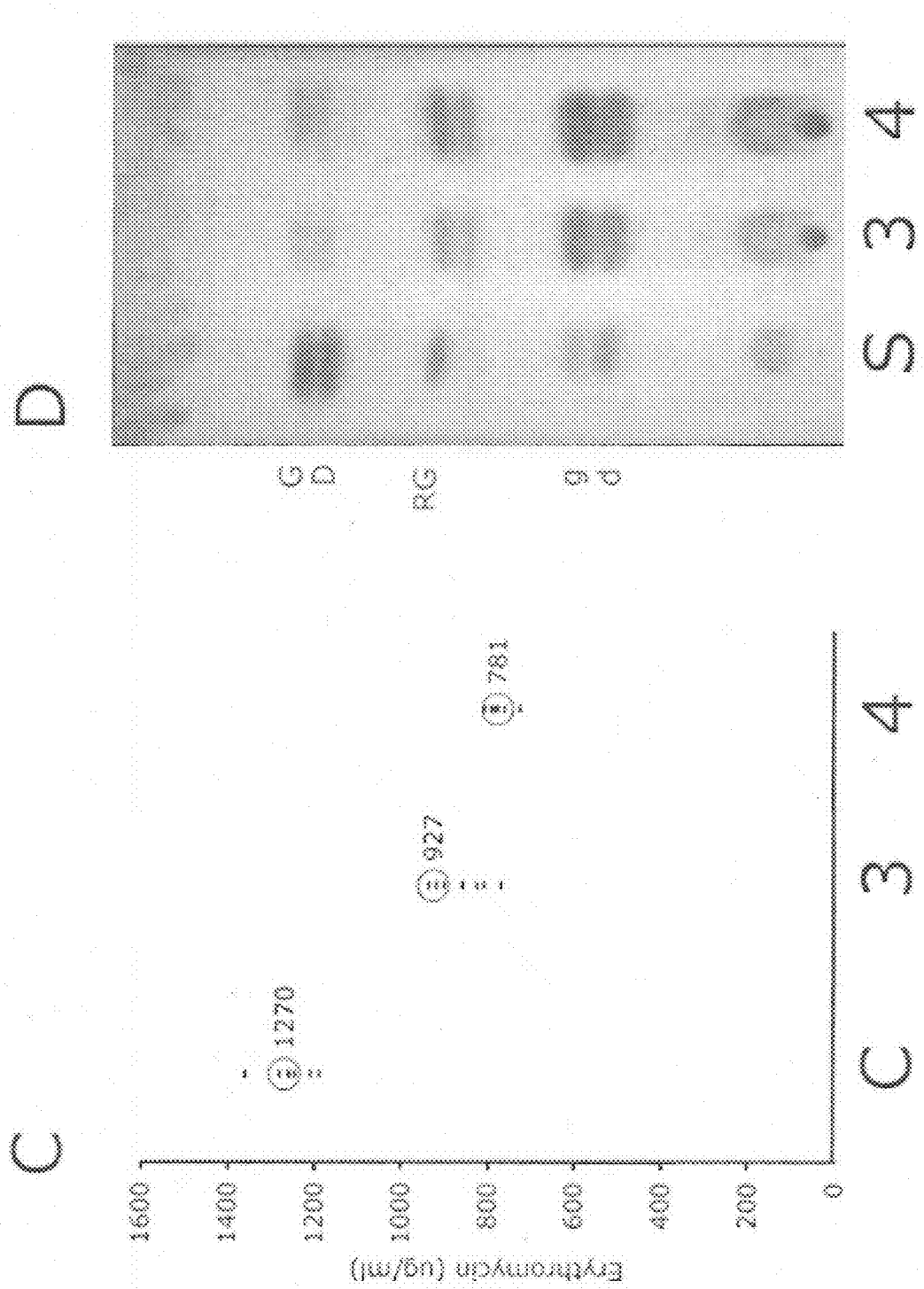
Figure 3C,D

95% ethanol extraction method
Isoflavone recovery and purity from 132 g soy flour

|  | Ppt 1 | Ppt 2 | Total |
|---|---|---|---|
| mg | 22 | 20 | 42 |
| % recovery | 13 | 12 | 25 |
| % purity | 44 | 41 | 43 |

Data Ref: ISO34

Figure 6 C

Exp 3. Ethylacetate method
Isoflavone recovery and purity from 22 g soy flour

|            | Ppt 1 | Ppt 2 | Total |
|------------|-------|-------|-------|
| mg         | 10.6  | 3.1   | 13.7  |
| % recovery | 37    | 11    | 48    |
| % purity   | 85    | 71    | 80    |

Data Ref: ISO36

Figure 8 C

SOYBEAN-BASED FERMENTATION MEDIA, METHODS OF MAKING AND USE

CROSS-REFERENCE TO RELATED APPLICATIONS

This application is a Divisional of U.S. patent application Ser. No. 12/768,425, filed Apr. 27, 2010 and incorporated herein by reference in its entirety, which claims the benefit of priority to U.S. Provisional Application Ser. No. 61/173,662, filed Apr. 29, 2009, which is incorporated by reference herein in its entirety.

STATEMENT REGARDING FEDERALLY SPONSORED RESEARCH OR DEVELOPMENT GOVERNMENTAL SUPPORT

This invention was made with Government support under Grant No. CA093165 awarded by the National Cancer Institute and by the U.S. Small Business Administration Office of Technology Small Business Innovation Research Program. The government has certain rights to this invention.

BACKGROUND OF THE INVENTION

The manufacture of bulk pharmaceuticals such as antibiotics is a competitive high-volume, low-profit enterprise, and co-product recovery is one method for increasing the profitability of this process. Many large scale pharmaceutical manufacturers use soybean meal to support the growth and secondary metabolite production of their fermentation microorganisms. For example, soybean meal is a common medium component of many pharmaceutical fermentations, including the erythromycin fermentation. Soybean flour contains isoflavones, which are valuable nutraceutical compounds. Leguminous plants such as soybean are also a rich source of isoflavones, a group of valuable compounds that can confer a variety of health benefits when consumed (Kaufman et al., Journal of Alternative and Complementary Medicine, 3(1):7-12, 1997). Legumes typically contain isoflavone glucosides as well as the isoflavones daidzein and/or genistein. It is the aglycone forms of isoflavones such as daidzein or genistein, referred to here as isoflavones, that are the primary biologically active compounds that confer health benefits when consumed. Purified isoflavones can also be used as intermediates in the synthesis of potential derivatives that can be used as drugs. At present purified genistein can cost up to about $2,370 a gram. Thus, a cost-effective isoflavone co-product recovery method would benefit soybean-based fermentation operations.

A previous study investigating isoflavone recovery focused on recovery of isoflavones from spent fermentation broth (U.S. patent application Ser. No. 11/464,700). In the study, it was found that isoflavones were not destroyed during the fermentation as originally thought (Hessler et al., Appl. Microbiol Biotechnol, 47:398-404, 1997), but were converted into biotransformation products during the fermentation. Thus, this approach offered the first practical isoflavone recovery method for industrial soybean-based fermentations. However, several problems made this isoflavone co-product recovery approach less than ideal. One problem was that isoflavone biotransformation products must be converted back into their aglycone counterparts by acid hydrolysis in order to recover the desired form of the isoflavones. Another problem was that the isoflavone extract from treated spent fermentation broth would likely contain a wide array of contaminating compounds. Contaminants reduce the quality and marketability of the product unless the isoflavones are more highly purified, thereby introducing additional time and expense into the recovery process. The market for the highly purified crystalline isoflavones, however, is smaller than the market for more simply obtained concentrated isoflavone extracts.

It has been reported that the genistein in soybean flour might be responsible for the induction of desirable cytochrome P-450 enzymes of *Streptomyces griseus* during fermentation of that organism (Sariaslani and Kunz, Biochem Biophys Res Commun. 141(2):405, 1986).

U.S. Pat. Nos. 5,320,949, 5,352,384, 5,637,561, and 5,637,562, each of which are incorporated herein by reference in their entireties, disclose methods for preparing isoflavone aglycone enriched soybean products.

Canadian Patent 02240795 discloses vegetable protein compositions containing an isoflavone depleted vegetable protein material with an isoflavone containing material dispersed therein and processes for producing the compositions.

Because of the widespread use of isoflavone-rich soybean-based fermentation media in the high-volume, low-profit manufacture of bulk pharmaceuticals, isoflavone co-product recovery is important for increasing the profitability of this process. Accordingly, a need still exists for soybean-based fermentation media that will support microorganism fermentation following co-product recovery.

SUMMARY OF THE INVENTION

The invention generally provides fermentation media and methods of making fermentation media.

In certain aspects, the invention provides a fermentation medium comprising: i) an isoflavone-depleted soybean meal or isoflavone-depleted soybean meal product and ii) at least one exogenous added ingredient that comprises a substrate for microbial growth. In certain embodiments, the fermentation medium can comprise: i) an isoflavone-depleted soybean meal or isoflavone-depleted soybean meal product and ii) at least one exogenous added ingredient that comprises a substrate for microbial growth, wherein the isoflavone content of the fermentation media is less than that of a control fermentation media comprising an equivalent amount of soybean meal or soybean meal product. In certain embodiments, the exogenous added ingredient comprises one or more of a monosaccharide, a disaccharide, a polysaccharide, a plant oil, and/or a corn steep liquor. In certain embodiments, at least one of the ingredients is selected from the group consisting of glucose, fructose, sucrose, and combinations thereof. In certain embodiments, the isoflavone-depleted soybean meal or isoflavone-depleted soybean meal product is obtained by treating soybean meal or a soybean meal product with at least one agent that converts an isoflavone glucoside to an isoflavone and extracting the treated soybean meal or treated soybean meal product with a water immiscible solvent. In certain embodiments, the isoflavone-depleted soybean meal or isoflavone-depleted soybean meal product is obtained by extracting soybean meal or a soybean meal product with a water immiscible solvent or a water miscible solvent. In certain embodiments, the medium supports a fermentation product yield equivalent to, or greater than, a fermentation product yield supported by a control fermentation medium comprising soybean meal or soybean meal product and at least one exogenous added ingredient that comprises a substrate for microbial growth. In certain embodiments, the fermentation product is a drug or drug precursor. In certain embodiments, the isoflavone-depleted soybean meal or isoflavone-depleted soybean meal product is provided at about 10 grams per liter (weight/volume) to about 40 grams per liter (weight/volume). In certain embodiments, the isoflavone-depleted soybean meal or isoflavone-depleted soybean meal product is provided at about 15 grams per liter (weight/volume) to about 25 grams per liter (weight/volume). In certain embodiments, the isoflavone-depleted soybean meal or isoflavone-depleted soybean meal product is at about 15 grams per liter (weight/volume) to about 25 grams per liter (weight/volume), polysaccharides are at about 10 to about 20 grams per liter, calcium carbonate is at about 1 to about 5 grams per liter, magnesium sulfate is provided as a heptahydrate at about 0.1 to about 1 gram per liter, iron sulfate is provided as a heptahydrate at about 10 to about 20 milligrams per liter, and plant oil is at about 40 to about 60 milliliters per liter. In certain embodiments, a total isoflavone aglycone content of the fermentation media is less than about 125 milligrams total isoflavone aglycones per liter of fermentation media.

In other aspects, the invention provides methods of making a fermentation medium comprising an isoflavone-depleted soybean meal or isoflavone-depleted soybean meal product, the method comprising the steps of: a) treating soybean meal or a soybean meal product with at least one agent that converts an isoflavone glucoside to an isoflavone aglycone; b) extracting the treated soybean meal or soybean meal product with a water immiscible solvent to obtain an isoflavone-depleted soybean meal or isoflavone-depleted soybean meal product; and, c) combining the treated and extracted isoflavone-depleted soybean meal or isoflavone-depleted soybean meal product with at least one exogenous added ingredient that comprises a substrate for microbial growth. In certain embodiments, the water immiscible solvent comprises ethyl acetate, propyl acetate, butyl acetate, amyl acetate, cyclohexanol, n-butanol, iso-butanol, tert-butanol, amyl alcohol, a water immiscible ketone, a water immiscible aldehyde, carbon tetrachloride, chloroform, cyclohexane, 1,2-dichloroethane, dichloromethane, diethyl ether, dimethyl formamide, heptane, hexane, methyl-tert-butyl ether, pentane, toluene, 2,2,4-trimethyl pentane, or a combination thereof. In certain embodiments, the agent that converts an isoflavone glucoside to an isoflavone comprises an acid, one or more enzymes wherein at least one of the enzymes exhibits a beta-glucosidase activity, or a combination thereof. In certain embodiments, the method further comprises the step of recovering one or more isoflavone aglycones from the solvent used to extract the treated soybean meal or treated soybean meal product. In certain embodiments, the medium supports a fermentation product yield equivalent to, or greater than, a fermentation product yield supported by a control fermentation medium comprising soybean meal or soybean meal product and at least one exogenous added ingredient that comprises a substrate for microbial growth. In certain embodiments, the exogenous added ingredient comprises one or more of a monosaccharide, a disaccharide, a polysaccharide, a plant oil, and/or corn steep liquor. In certain embodiments, the methods provide for a fermentation medium comprising an isoflavone-depleted soybean meal or isoflavone-depleted soybean meal product that has a total isoflavone aglycone content of less than about 125 milligrams total isoflavone aglycones per liter. Also provided are embodiments of any of the aforementioned methods, wherein the treated and extracted isoflavone-depleted soybean meal or isoflavone-depleted soybean meal product is obtained as an aqueous fraction in step (b) and wherein said aqueous fraction is combined with at least one exogenous added ingredient in step (c).

Another aspect of the invention provides fermentation media made by any of the aforementioned methods.

A further aspect of the invention provides methods of making a fermentation medium comprising an isoflavone-depleted soybean meal or isoflavone-depleted soybean meal product, where the methods comprise the steps of: a) extracting soybean meal or soybean meal product with a water miscible solvent or a water immiscible solvent to obtain an isoflavone-depleted soybean meal or isoflavone-depleted soybean meal product; and b) combining the extracted isoflavone-depleted soybean meal or isoflavone-depleted soybean meal product with at least one exogenous added ingredient that comprises a substrate for microbial growth. In certain embodiments, the water miscible solvent comprises water, methanol, ethanol, n-propanol, isopropanol, acetone, acetonitrile, dimethyl sulfoxide, 1,4-dioxane, a water miscible ketone, a water miscible aldehyde, or a combination thereof. In certain embodiments, the water immiscible solvent comprises ethyl acetate, propyl acetate, butyl acetate, amyl acetate, cyclohexanol, n-butanol, iso-butanol, tert-butanol, amyl alcohol, a water immiscible ketone, a water immiscible aldehyde, carbon tetrachloride, chloroform, cyclohexane, 1,2-dichloroethane, dichloromethane, diethyl ether, dimethyl formamide, heptane, hexane, methyl-tert-butyl ether, pentane, toluene, 2,2,4-trimethyl pentane, or a combination thereof. In certain embodiments, the water miscible solvent comprises at least about 50% ethanol by volume and no more than about 50% water by volume. In certain embodiments, the solvent comprises at least about 85% ethanol by volume and no more than about 15% water by volume. In certain embodiments, the solvent comprises at least about 95% ethanol by volume and no more than about 5% water by volume. In certain embodiments, the method further comprises the step of recovering one or more isoflavone glucosides from the water miscible solvent used to extract the soybean meal or isoflavone-depleted soybean meal product. In certain embodiments, the method further comprises conversion of the extracted isoflavone glucosides to isoflavone aglycones. In certain embodiments, the medium supports a fermentation product yield equivalent to, or greater than, a fermentation product yield supported by a control fermentation medium comprising i) soybean meal or a soybean meal product and ii) at least one exogenous added ingredient that comprises a substrate for microbial growth. In certain embodiments, the exogenous added ingredient comprises one or more of a monosaccharide, a disaccharide, a polysaccharide, a plant oil, and/or corn steep liquor. In certain embodiments, the methods provide for a fermentation medium comprising an isoflavone-depleted soybean meal or isoflavone-depleted soybean meal product that has a total isoflavone aglycone content of less than about 125 milligrams total isoflavone aglycones per liter.

A further aspect of the invention provides fermentation media made by any of the aforementioned methods.

Another aspect of the invention provides a method of obtaining at least one fermentation product, the method comprising the steps of: a) culturing a microorganism in a fermentation medium comprising an isoflavone-depleted soybean meal or isoflavone-depleted soybean meal product and at least one exogenous added ingredient that comprises a substrate for microbial growth; and b) isolating a fermentation product from a culture wherein the culture comprises a fermentation broth and the microorganism from step (a), thereby obtaining at least one fermentation product. In certain embodiments, the microorganism is an *Actinomycete*, a *Bacillus*, a *Staphylococcus*, or a fungus. In certain embodiments, the actinomycete is selected from the group consisting of *Streptomyces, Streptosporangium, Actinoplanes, Micromonospora, Geodermatophilus, Nocardioides, Saccharothrix, Amycolatopsis, Kutzneria, Saccharomonospora,*

*Saccharopolyspora, Kitasatospora, Microbispora, Actinomadura*, and *Saccharopolyspora*. In certain embodiments, the actinomycete is selected from the group consisting of *Streptomyces rimosus, Streptomyces fradiae, Streptomyces hygroscopicus, Streptomyces cinnamonensis, Streptomyces peucetius, Saccharopolyspora erythraea, Streptomyces avermitilis, Streptomyces glaucescens, Streptomyces violaceoniger, Streptomyces kanamyceticus, Streptomyces clavuligerus*, and *Streptomyces roseolous*. In certain embodiments, the actinomycete is *Saccharopolyspora erythraea*. In certain embodiments, at least one of the fermentation products is a drug, a drug precursor, or a pesticide. In certain embodiments, the drug is antibiotic, an animal growth modulator, an anticancer agent, an immunosuppressant, an anti-hypertensive agent, or an anti-parasitic agent. In certain embodiments, the pesticide is an insecticide. In certain embodiments, the drug or a drug precursor is selected from the group consisting of oleandomycin, actinomycin, avermectin, lasalocid, tetracenomycin, tetracycline, oxytetracycline, tylosin, rapamycin, daunorubicin, rifamycin, monensin, and erythromycin. In certain embodiments, the drug or drug precursor is erythromycin and the actinomycete is *Saccharopolyspora erythraea*. In certain embodiments, the fermentation products is a fermentation broth. In certain embodiments, the fermentation broth is used to make a feed additive. In certain embodiments, the fermentation product is a cultured microorganism from step (b). In certain embodiments, the at least one exogenous added ingredient that comprises a substrate for microbial growth comprises one or more of a monosaccharide, a disaccharide, a polysaccharide, a plant oil, and/or corn steep liquor. In certain embodiments, at least one of the ingredients is selected from the group consisting of glucose, fructose, sucrose, and combinations thereof. In certain embodiments, the isoflavone-depleted soybean meal or isoflavone-depleted soybean meal product is obtained by treating soybean meal or a soybean meal product with at least one agent that converts an isoflavone glucoside to an isoflavone and extracting the treated soybean meal or soybean meal product with a solvent. In certain embodiments, the isoflavone-depleted soybean meal or isoflavone-depleted soybean meal product is obtained by extracting soybean meal or a soybean meal product with a solvent. In certain embodiments, the method provides a fermentation product yield equivalent to, or greater than, a fermentation product yield supported by a control fermentation medium comprising soybean meal or a soybean meal product and at least one exogenous added ingredient that comprises a substrate for microbial growth. In certain embodiments, the methods use a fermentation medium comprising an isoflavone-depleted soybean meal or isoflavone-depleted soybean meal product that has a total isoflavone aglycone content of less than about 125 milligrams total isoflavone aglycones per liter. In certain embodiments of any of the aforementioned methods, the fermentation media comprises ethanol or ethyl acetate. In certain embodiments where the isoflavone-depleted soybean meal or isoflavone-depleted soybean meal product is obtained by extracting soybean meal or a soybean meal product with a solvent, the fermentation media comprises ethanol or ethyl acetate. In certain embodiments of any of the aforementioned methods, the fermentation media comprises ethanol is at a concentration of about 1% to about 2%. In certain embodiments, where the method provides a fermentation product yield equivalent to, or greater than, a fermentation product yield supported by a control fermentation medium, the fermentation media comprises ethanol at a concentration of about 1% to about 2% or the fermentation media comprises ethyl acetate at a concentration of about 2% to about 6%. In certain embodiments, where the method provides a fermentation product yield equivalent to, or greater than, a fermentation product yield supported by a control fermentation medium, the fermentation media comprises ethyl acetate at a concentration of about 2% to about 6%.

Another aspect of the invention provides fermentation broths obtained by any of the aforementioned methods of obtaining a fermentation product.

A further aspect of the invention provides a feed additive produced from a fermentation broth obtained by any of the aforementioned methods of obtaining a fermentation product any of the aforementioned methods of obtaining a fermentation product.

Also provide herein are methods of obtaining at least one fermentation product comprising the steps of: a. culturing a microorganism in a fermentation medium comprising soybean meal or soybean meal product and either: i) ethanol is at a concentration of about 1% to about 2%; or, ii) ethyl acetate at a concentration of about 2% to about 6%; and b. isolating a fermentation product from a culture wherein said culture comprises a fermentation broth and said microorganism from step (a), thereby obtaining at least one fermentation product. In certain embodiments of these methods, the microorganism is an *Actinomycete*, a *Bacillus*, a *Staphylococcus*, or a fungus. In certain embodiments of these methods, the *Actinomycete* is selected from the group consisting of *Streptomyces, Streptosporangium, Actinoplanes, Micromonospora, Geodermatophilus, Nocardioides, Saccharothrix, Amycolatopsis, Kutzneria, Saccharomonospora, Saccharopolyspora, Kitasatospora, Microbispora*, and *Actinomadura*. In certactinomycete is selected from the group consisting of *Streptomyces rimosus, Streptomyces fradiae, Streptomyces hygroscopicus, Streptomyces cinnamonensis, Streptomyces peucetius, Saccharopolyspora erythraea, Streptomyces avermitilis, Streptomyces glaucescens, Streptomyces violaceoniger, Streptomyces kanamyceticus, Streptomyces clavuligerus*, and *Streptomyces roseolous*. In certain embodiments of the methods, the *Actinomycete* is *Saccharopolyspora erythraea*. In certain embodiments of the methods, at least one of the fermentation products is a drug, a drug precursor, or a pesticide. In certain embodiments of the methods, the drug is an antibiotic, an animal growth modulator, an anti-cancer agent, an immunosuppressant, an anti-hypertensive agent, or an anti-parasitic agent and wherein said pesticide is an insecticide. In certain embodiments of the methods, the drug or a drug precursor is selected from the group consisting of oleandomycin, actinomycin, avermectin, lasalocid, tetracenomycin, tetracycline, oxytetracycline, tylosin, rapamycin, daunorubicin, rifamycin, monensin, and erythromycin. In certain embodiments of the methods, the drug or drug precursor is erythromycin and the *Actinomycete* is *Saccharopolyspora erythraea*.

BRIEF DESCRIPTION OF THE DRAWINGS

FIG. 1 shows the effects of isoflavone-depleted soybean flour on erythromycin production in five day shake flask fermentations using OFM1 medium. Panel A erythromycin production: Lane 1, natural (i.e. control) soybean flour (untreated); lane 2, ethyl acetate extracted soybean flour; lane 3, beta-glucosidase treated soybean flour; lane 4, beta-glucosidase treated and ethyl acetate extracted soybean flour. G, genistein; D, daidzein; RG, rhamnosylgenistein; g, genistin, d, daidzin. Panel B. TLC analysis of untreated soybean flour (lane 5) and beta-glucosidase treated soybean flour (lane 6). S contains isoflavone standards for: G, genistein; D, daidzein; RG, rhamnosylgenistein; g, genistin, d, daidzin.

FIG. 2 shows the effects of isoflavone-depleted soybean flour on erythromycin production. FIG. 2, Panel A, erythromycin production: Lane 1, control soybean flour, no extraction; lane 2, isoflavone-depleted soybean flour, ethyl acetate extraction; lane 3, isoflavone-depleted soybean flour, 95% ethanol extraction; and lane 4, isoflavone-depleted soybean flour, 50% aqueous ethanol extraction). FIG. 2, Panel B, TLC analysis of soybean flour extracts: lane 5, ethyl acetate; lane 6, 95% ethanol; lane 7, methanol; and lane 8, n-propanol. S contains standards for: G, genistein; D, daidzein; RG, rhamnosylgenistein; g, genistin, d, daidzin.

FIG. 3 shows results of the stirred ethanol extraction method. Panel A, erythromycin production: Lane C, control soybean flour, no treatment; lane 1, 2 hr extraction with 95% ethanol; lane 2, 12 hr extraction with 95% ethanol. Panel B, TLC analysis of soybean flour extracts: Lane S, isoflavone reference standards; lane 1, 2 hr extraction with 95% ethanol; lane 2, 12 hr extraction with 95% ethanol. Panel C, erythromycin production: Lane C, erythromycin production, control soybean flour, no treatment; lane 3, 2 hr extraction with 50% ethanol; lane 4, 12 hr extraction with 50% ethanol. Panel D, TLC analysis of soybean flour extracts: Lane S, isoflavone reference standards; lane 1, 2 hr extraction with 50% ethanol; lane 2, 12 hr extraction with 50% ethanol. S lanes contain isoflavone standards for: G, genistein; D, daidzein; RG, rhamnosylgenistein; g, genistin, d, daidzin.

DETAILED DESCRIPTION

Figure 4:
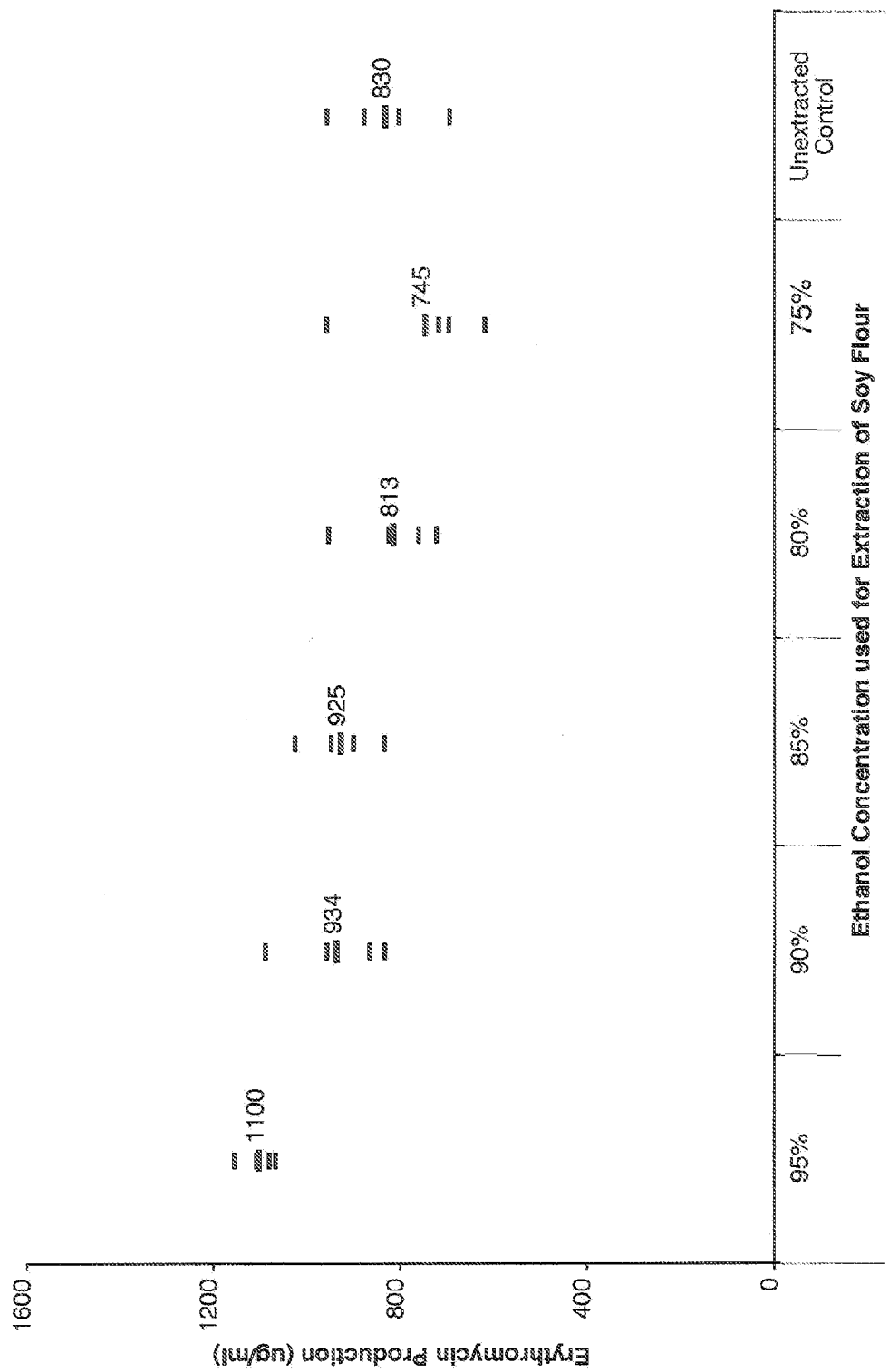
FIG. 4 shows the effect of the ethanol extraction method on the erythromycin fermentation. Five different ethanol: distilled water concentrations were used to extract soy flour. The unextracted control is soy flour that had not received any treatment prior to its use in the erythromycin fermentation.

Because of the inherent contamination problems of recovering a partially purified nutraceutical extract from spent fermentation broth, an alternative method of recovering isoflavones from the fermentation process was investigated. In brief, this alternative strategy involved an initial extraction of isoflavones from the soybean meal or soybean meal product to produce an isoflavone-depleted soybean meal or isoflavone-depleted soybean meal product an a valuable co-product (i.e. isoflavones). Isoflavone-depleted soybean meal or soybean meal product can then be combined with other exogenous ingredients that include, but are not limited to, one or more substrates for microbial growth, to obtain an fermentation media comprising an isoflavone-depleted soybean meal or isoflavone-depleted soybean meal product. In certain embodiments, a fermentation media comprising an isoflavone-depleted soybean meal or isoflavone-depleted soybean meal product can be used in a fermentation process to obtain fermentation product yields that are equivalent to or greater than the yields obtained when control soybean meal or soybean meal products (i.e. soybean meal or soybean meal products that have not been treated to deplete isoflavones) are used in the fermentation.

DEFINITIONS

As used herein, the phrase "drug precursor" refers to any compound produced in a fermentation process that is used in any subsequent processes to produce a drug or is any compound that is a pro-drug. A drug precursor can thus be a compound that is a drug (i.e., erythromycin) that is converted to other derived drugs by other subsequent processes.

As used herein, the terms "extracting", when used in the context of treating a soybean meal or soybean meal product with a water miscible solvent or a water immiscible solvent to remove isoflavones, refers to one or more rounds of solvent treatment. Multiple rounds of solvent treatment can be used in instances where greater degrees of isoflavone depletion are desired.

As used herein, the term "isoflavone" refers to any of an isoflavone glucoside, an isoflavone aglycone, or a combination thereof. Isoflavone glucosides include, but are not limited to, genistin and daidzin. Isoflavone aglycones include, but are not limited to, genistein, daidzein, biochanin, formononetin, and glycitein.

As used herein, the phrase "total isoflavone aglycone(s)" refers to the combined aggregate of daidzein, genistein, and glycitein in a sample.

As used herein, the term "soybean meal" refers to any or all of the material obtained from a soybean from which oil has been removed.

A "soybean meal product" is any material obtained from soybean meal. Soybean meal products thus include, but are not limited to, dehulled soybean meal, soybean flour, and soybean grits.

Introduction

Because of the inherent contamination problems of recovering a partially purified nutraceutical extract from spent fermentation broth, an alternative method of recovering isoflavones from the fermentation process was investigated. In brief, this alternative strategy involved an initial extraction of isoflavones from the soybean meal or soybean meal product to produce an isoflavone-depleted soybean meal or isoflavone-depleted soybean meal product and a valuable co-product (i.e. isoflavones). Isoflavone-depleted soybean meal or isoflavone-depleted soybean meal product can then be combined with other exogenous ingredients that include, but are not limited to, one or more substrates for microbial growth, to obtain an fermentation media comprising an isoflavone-depleted soybean meal or isoflavone-depleted soybean meal product. In certain embodiments, a fermentation media comprising an isoflavone-depleted soybean meal or isoflavone-depleted soybean meal product can be used in a fermentation process to obtain fermentation product yields that are equivalent to or greater than the yields obtained when control soybean meal or soybean meal products (i.e. soybean meal or soybean meal products that have not been treated to deplete isoflavones) are used in the fermentation.

Isoflavone-Depleted Soybean-Based Fermentation Media

As used herein, the term "isoflavone-depleted", when used in reference to a soybean meal or soybean meal product, refers to a soybean meal or soybean meal product wherein at least 10% of the isoflavones on a weight/weight basis in the soybean meal or soybean meal product have been removed. In certain embodiments, at least 20%, at least 30%, at least 40%, at least 50%, at least 60%, at least 70%, at least 80%, at least 90%, or at least 95% of the isoflavones on a weight/weight basis are removed from a soybean meal or soybean meal product to obtain an isoflavone-depleted soybean meal or isoflavone-depleted soybean meal product used in a fermentation media provided herein. In this context, the term "isoflavones" refers to the combined aggregate of both isoflavone glucosides and isoflavone aglycones present in a soybean meal or soybean meal product.

Isoflavone-depleted soybean meal or isoflavone depleted soybean meal products can be provided in a fermentation media at any concentration that provides for fermentation product recovery. In certain embodiments, isoflavone-depleted soybean meal or isoflavone depleted soybean meal products are provided at any of about 5 grams per liter (weight/volume) to about 60 grams per liter (weight/volume) fermentation media, about 10 grams per liter (weight/volume) to about 40 grams per liter (weight/volume) fermentation media, about 15 grams per liter (weight/volume) to about 25 grams per liter (weight/volume) fermentation media, or about 20 grams per liter (weight/volume) to about 25 grams per liter (weight/volume) fermentation media.

The isoflavone content of the fermentation media provided herein which comprises an isoflavone-depleted soybean meal or isoflavone depleted soybean meal product is less than the isoflavone content of a control fermentation media comprising an equivalent amount of soybean meal or soybean meal product. The total isoflavone aglycone content of the fermentation media provided herein which comprises an isoflavone-depleted soybean meal or isoflavone depleted soybean meal product is also less than the total isoflavone aglycone content of a control fermentation media comprising an equivalent amount of soybean meal or soybean meal product. Thus, a fermentation media provided herein which comprises an isoflavone-depleted soybean meal or isoflavone depleted soybean meal product provided at about 5 grams per liter (weight/volume) to about 60 grams per liter (weight/volume) will have a total isoflavone aglycone content that is less than that of a control fermentation medium comprising soybean meal or soybean meal product at about 5 grams per liter (weight/volume) to about 60 grams per liter (weight/volume), respectively. The fermentation media provided herein that comprises isoflavone depleted soybean meal or isoflavone depleted soybean meal product can in certain embodiments have a total isoflavone aglycone content of less than about 175 milligrams of total isoflavone aglycones per liter of fermentation media. In still other embodiments, the fermentation media provided herein can in certain embodiments have a total isoflavone aglycone content of less than about 155 milligrams, 130 milligrams, 125 milligrams, 120 milligrams, 115 milligrams, 100 milligrams, 95 milligrams, 75 milligrams, 55 milligrams, 35 milligrams, 15 milligrams, or 7.5 milligrams of total isoflavone aglycones per liter of fermentation media. In still other embodiments, the fermentation media provided herein can have a total isoflavone aglycone content of less than about 6 milligrams, 3 milligrams, 2 milligrams, 1 milligrams, 0.5 milligrams, or 0.15 milligrams of total isoflavone aglycones per liter of fermentation media. Total isoflavone aglycone content of a fermentation media can be determined directly by any suitable analytic method. Total isoflavone aglycone content can also be readily estimated based on the amount of isoflavone-depleted soybean meal or isoflavone depleted soybean meal product provided in the media, the percentage of total isoflavone aglycones depleted, and the total isoflavone aglycone content of the soybean meal or soybean meal product used. The United States Department of Agriculture indicates that the total isoflavone aglycone content (i.e. combined daidzein, genistein, and glycitein content) of various soy flours can vary between about 0.6 milligrams total isoflavones per gram soy flour to about 3.25 milligrams per gram soy flour (see USDA Database for the Isoflavone Content of Selected Foods, Release 2.0, September 2008, located on the world wide web at www.ars.usda.gov/SP2UserFiles/Place/12354500/Data/isoflav/Iasoflav_R2.pdf).

To obtain a fermentation medium comprising an isoflavone-depleted soybean meal or isoflavone-depleted soybean meal product, at least one ingredient from an exogenous source (i.e. a source other than the isoflavone depleted soybean meal or soybean meal product) that is a substrate for microbial growth is added to the isoflavone depleted soybean meal or soybean meal product. Substrates for microbial growth can comprise any material used by a microorganism as either a carbon source, a nitrogen source, or a combined carbon-nitrogen source. In certain embodiments, a monosaccharide, a disaccharide, a polysaccharide, or a combination thereof from one or more exogenous source(s) can be added to the isoflavone depleted soybean meal or soybean meal product. Polysaccharides used can include, but are not limited to, soluble starch, dextrin, corn starch, and combinations thereof. In certain embodiments, polysaccharides can be provided in a fermentation media either individually or in aggregate at concentrations of about 1 g/L to about 60 g/L. Certain embodiments can thus comprise any of 1 g/L to about 60 g/L of a monosaccharides-, disaccharides-, or polysaccharides that include, but are not limited to, soluble starch, starch, or dextrin Certain embodiments can also thus comprise any of 1 g/L to about 60 g/L total of a monosaccharides-, disaccharides-, or polysaccharides that include, but are not limited to, soluble starch, starch, or dextrin. In certain embodiments, a plant oil can be added to the fermentation. Plant oils used can include, but are not limited to, coconut oil, corn oil, cottonseed oil, olive oil, palm oil, peanut oil, rapeseed oil, safflower oil, sesame oil, soybean oil, sunflower oil, and combinations thereof. Corn steep liquor can also be included in a fermentation media as a substrate for microbial growth. In certain embodiments, such plant oils can be provided either individually or in aggregate at any of about 1 ml/L to about 60 ml/L in a fermentation media provided herein.

Fermentation media comprising an isoflavone-depleted soybean meal or isoflavone-depleted soybean meal product and at least one ingredient from an exogenous source that is a microbial growth substrate can also comprise a variety of other ingredients from an exogenous source. In certain embodiments, various mineral salts that include, but are not limited to, sodium chloride, calcium carbonate, magnesium sulfate, ammonium salts, potassium salts, phosphate salts, and/or iron sulfate can be added to the fermentation media. Sodium chloride can be added at a concentration of about 1 gram per liter to about 12 grams per liter (weight volume) or at a concentration of about 2 grams per liter to about 8 grams per liter (weight volume) in certain embodiments. Calcium carbonate can be added at a concentration of about 1 gram per liter to about 12 grams per liter (weight volume) or at a concentration of about 2 grams per liter to about 8 grams per liter (weight volume) in certain embodiments. In certain embodiments, trace elements including of iron, borate, zinc, copper, molybdenum, manganese, iodine, and/or cobalt can be added to the fermentation media at concentrations conducive to microbial growth.

It is anticipated that isoflavone-depleted soybean meal or isoflavone-depleted soybean meal product can be substituted for control soybean meal or control soybean meal product in a other conventional soybean-based fermentation media that have been disclosed to obtain a fermentation media of this invention that comprises an isoflavone-depleted soybean meal or isoflavone-depleted soybean meal product. Thus, an isoflavone-depleted soybean meal product (soybean flour) can be substituted for control soybean meal or control soybean meal product in any of a V1 media, a V2 media, a F1 media (all disclosed by Minas et al., Biotechnol. Prog. 14, 561, 1998), or a substantial equivalent thereof. Thus, a fermentation media provided herein can comprise about 14 g/L to about 18 g/L corn starch, about 9 g/L to about 11 g/L dextrin, about 10 g/L to about 20 g/L isoflavone-depleted soybean flour, about 1 g/L to about 4 g/L sodium chloride, about 3 ml/L to about 7 mL/L corn steep liquor, about 0.5 g/L to about 2.0 g/L ammonium sulfate, and about 4 mL/L to about 8 mL/L soybean oil, and about 2 g/L to about 6 g/L calcium carbonate. In certain embodiments, a fermentation media provided herein can comprise about 14 g/L to about 18 g/L corn starch, about 9 g/L to about 11 g/L dextrin, about 10 g/L to about 20 g/L isoflavone-depleted soybean flour, about 1 g/L to about 4 g/L sodium chloride, about 3 ml/L to about 7 mL/L corn steep liquor, about 0.5 g/L to about 2.0 g/L ammonium sulfate, and about 4 mL/L to about 8 mL/L soybean oil, and about 2 g/L to about 6 g/L calcium carbonate. In certain embodiments, a fermentation media provided herein can comprise about 14 g/L to about 22 g/L corn starch, about 10 g/L to about 14 g/L dextrin, about 10 g/L to about 20 g/L isoflavone-depleted soybean flour, about 1 g/L to about 5 g/L sodium chloride, about 4 mL/L to about 8 mL/L corn steep liquor, about 0.5 g/L to about 2 g/L ammonium sulfate, about 4 mL/L to about 8 mL/L soybean oil, and about 3 g/L to about 7 g/L calcium carbonate. In still other embodiments, a fermentation media provided herein can comprise about 30 g/L to about 40 g/L corn starch, about 24 g/L to about 40 g/L dextrin, about 25 g/L to about 40 g/L isoflavone-depleted soybean flour, about 5 g/L to about 10 g/L sodium chloride, about 15 mL/L to about 25 mL/L corn steep liquor, about 1 g/L to about 5 g/L ammonium sulfate, about 2 mL/L to about 10 g/L soybean oil, and about 4 g/L to about 10 g/L calcium carbonate. In still other embodiments, a fermentation media provided herein can comprise about 15 g/L to about 30 g/L isoflavone depleted soybean meal or isoflavone depleted soybean product, about 1 g/L to about 20 g/L soluble starch, about 1 g/L to about 5 g/L calcium carbonate, about 0.1 g/L to about 1 g/L magnesium sulfate heptahydrate, about 10 mg/L to about 20 mg/L iron sulfate heptahydrate, and about 30 ml/L to about 60 ml/L Soybean oil. In certain embodiments, the pH of any of the aforementioned media can be adjusted to about pH 6.4 to about pH 6.9.

Methods of Making Fermentation Media Comprising an Isoflavone-Depleted Soybean Meal or Isoflavone-Depleted Soybean Meal Product A variety of methods of extracting isoflavones from soybean meal or soybean meal products can be used to obtain isoflavone depleted soybean meal or isoflavone depleted soybean meal products for use in fermentation media are provided herein.

One method of obtaining isoflavone-depleted soybean meal or isoflavone-depleted soybean meal product involves treating soybean meal or a soybean meal product with at least one agent that converts an isoflavone glucoside to an isoflavone aglycone, extracting said treated soybean meal or soybean meal product with a water immiscible solvent; and separating the treated soybean meal or soybean meal product from the solvent that contains the isoflavone aglycones. Agents that can convert an isoflavone glucoside to an isoflavone aglycone include, but are not limited to, enzymes and compounds that provide for acidification of solutions comprising isoflavone glucosides.

Any enzyme, composition comprising an enzyme, or enzyme mixture that provides for conversion of an isoflavone glucoside to an isoflavone aglycone can be used. Such enzymes, compositions and mixtures include, but are not limited to, those comprising one or more enzymes with beta-glucosidase activity. In certain embodiments, an enzyme mixture with beta glucosidase activity can be combined with an esterase activity that converts the acetate and malonate conjugates to glucone isoflavones by removing the acetate and malonate groups from the isoflavone conjugates. Commercially available sources of beta glucosidase preparations include, but are not limited to, i) Biopectinase 100L, Biopectinase 300L, and Biopectinase OK 70L (Quest International, Sarasota, Fla.); ii) Lactase F i(Amano International Enzyme Co., Inc., Troy, Va.); iii) Lactozyme (Novo Industries, Enzyme Division, Novo Alle, DK-2880 Bagsvaerd, Denmark); and Beta Glucanase (Bio-Cat, Inc., Troy, Va.).

U.S. Pat. Nos. 5,320,949, 5,352,384, 5,637,561, and 5,637,562, each of which is incorporated herein by reference in their entireties, disclose methods for preparing isoflavone aglycone enriched soybean products. In these methods, isoflavone glucosides are extracted from the soybean starting material with an aqueous solvent (i.e. a water miscible solvent) and converted to the aglycone form with a glucosidase. However, the methods disclosed in these aforementioned patents entail precipitating the aglycone isoflavones in an aqueous solvent by adjusting the pH and then recovering precipitated isoflavone aglycones with the soybean material to obtain a soybean product enriched in aglucone isoflavones. Nonetheless, methods disclosed in those patents can be adapted to provide for an isoflavone-depleted soybean material by simply omitting the precipitation step and separating the aqueous solution containing the isoflavone aglycones (and any residual isoflavone glucosides) from the insoluble isoflavone depleted soybean material.

Compounds that provide for acidification and that can be used to convert an isoflavone glucoside to an isoflavone aglycone include, but not limited to, boric acid, benzoic acid, butyric acid, carbonic acid, citric acid, hydrobromic acid, hydrochloric acid, hydrofluoric acid, hydro iodic acid, lactic acid, malic acid, mandelic acid, nitric acid, propionic acid, sulfuric acid, oxalic acid, perchloric acid, phosphoric acid, phosphonic acid, pyrophosphoric acid, pyruvic acid, valeric acid, acetic acid and formic acid. Acidification to a pH of about 3.5 to about 5.0 is typically sufficient to convert some isoflavone glucosides to isoflavone aglycones. Conversion of an isoflavone glucoside to an isoflavone aglycone with acidifying agents can be further facilitated by use of heating steps. Exemplary heating steps include, but are not limited to, temperatures from about 80° C. to about 100° C.

Once the isoflavone glucosides are converted to isoflavone aglycones by the aforementioned methods, isoflavone-depleted soybean meal or isoflavone-depleted soybean meal product can be obtained by extracting the isoflavone aglycones with a water immiscible solvent. Such isoflavone aglycones will be partitioned into the water-immiscible solvent, which is then easily separated from the extracted and isoflavone depleted soybean meal or soybean meal product by sedimentation, centrifugation, and the like. Water immiscible solvents used can comprise ethyl acetate, propyl acetate, butyl acetate, amyl acetate, cyclohexanol, n-butanol, iso-butanol, tert-butanol, amyl alcohol, a water immiscible ketone, a water immiscible aldehyde, carbon tetrachloride, chloroform, cyclohexane, 1,2-dichloroethane, dichloromethane, diethyl ether, dimethyl formamide, heptane, hexane, methyl-tert-butyl ether, pentane, toluene, 2,2,4-trimethyl pentane, or a combination thereof. In certain embodiments, ethyl acetate is used. It is shown herein that ethyl acetate extraction process works very efficiently to extract the nonpolar aglycone forms of the isoflavones. Ethyl acetate also co-extracts very little else from the soybean flour, resulting in a very pure isoflavone product.

Another method for obtaining a isoflavone-depleted soybean meal or isoflavone-depleted soybean meal product provided herein entails direct extraction of isoflavone glucosides from soybean meal or soybean meal product with a water miscible solvent and separation of the extracted soybean meal or soybean meal product from the water miscible solvent containing isoflavone glucosides. Such water miscible solvents are advantageous as they can provide for more efficient depletion of isoflavone glucosides in the soybean meal or soybean meal product. Water miscible solvents include, but are not limited to, water, methanol, ethanol, n-propanol, iso-propanol, acetone, acetonitrile, dimethyl sulfoxide, 1,4-dioxane, a water miscible ketone, a water miscible aldehyde, or a combination thereof. Methods for extracting isoflavones from soybean meal or soybean meal products with alcohols that include, but not limited to methanol and ethanol, are disclosed in U.S. Pat. Nos. 5,670,632 and 5,679,806, which are incorporated herein by reference in their entireties. JP 05176756A discloses recovery of isoflavone derivatives from soybean based materials by extracting the soybean based material with 80% methanol. U.S. Pat. No. 4,428,876, incorporated herein by reference in it's entirety, discloses use of a dilute aqueous alkaline solution to extract isoflavones and other compounds from plant materials and can thus be adapted to obtain isoflavone-depleted soybean meal or isoflavone-depleted soybean meal product. In certain embodiments of any of the aforementioned methods, the water miscible solvent containing isoflavone glucosides that has been separated from the isoflavone-depleted soybean material can be treated with one or more agents that convert the isoflavone glucosides to obtain isoflavone aglycones as useful co-products. In certain embodiments, extraction is facilitated by settling or centrifugation. Extraction time periods by either method can be for any time period that provides for a desired degree of isoflavone-depletion.

In certain embodiments, the water miscible solvent comprises a mixture of water and ethanol. In certain embodiments, ethanol comprises at least 50% of the water/ethanol mixture on a volume/volume basis. However, in other embodiments, ethanol comprises at least 55%, at least 60%, at least 65%, at least 70%, at least 75%, at least 80%, at least 85%, at least 90%, at least 95%, or about 99% of the water/ethanol mixture on a volume/volume basis. Extraction of isoflavones from soybean meal or soybean meal products with alcohol/water mixtures including, but not limited to, ethanol/water mixtures, can be facilitated by heating at about 40° to about 70° C. or by heating at about 50° to about 60° C. In certain embodiments, ethanol extraction is facilitated by settling or centrifugation. In certain embodiments, ethanol extraction is facilitated by stirring or mixing. For certain embodiments where 50% ethanol/50% water is used and a fermentation product yield equivalent or greater than a control value (i.e. unextracted soybean-based fermentation product yield) are desired, extraction is preferably accomplished by settling or centrifugation. Extraction time periods by either method can be for any time period that provides for a desired degree of isoflavone-depletion. Certain embodiments thus entail at least 30 minutes, at least one hour, or at least two hours of extraction. Other embodiments entail about 30 minutes to about 24 hours of extraction, about 1 hour to about 12 hours of extraction, or about 2 to about 12 hours of extraction.

Another method for obtaining a isoflavone-depleted soybean meal or isoflavone-depleted soybean meal product provided herein entails extraction of isoflavone glucosides from soybean meal or a soybean meal product by a direct extraction with a water immiscible solvent and separation of the extracted soybean meal or soybean meal product from the water immiscible solvent containing isoflavones. Water immiscible solvents used can comprise ethyl acetate, propyl acetate, butyl acetate, amyl acetate, cyclohexanol, n-butanol, iso-butanol, tert-butanol, amyl alcohol, a water immiscible ketone, a water immiscible aldehyde, carbon tetrachloride, chloroform, cyclohexane, 1,2-dichloroethane, dichloromethane, diethyl ether, dimethyl formamide, heptane, hexane, methyl-tert-butyl ether, pentane, toluene, 2,2,4-trimethyl pentane, or a combination thereof. In certain embodiments, ethyl acetate is used. In certain embodiments, extraction is facilitated by settling or centrifugation. Extraction time periods by either method can be for any time period that provides for a desired degree of isoflavone-depletion.

Methods for Obtaining at Least One Fermentation Product with a Fermentation Media Comprising an Isoflavone-Depleted Soybean Meal or Isoflavone-Depleted Soybean Meal Product and Fermentation Products Obtained Therefrom Methods for using a fermentation media comprising an isoflavone-depleted soybean meal or isoflavone-depleted soybean meal product and at least one substrate for microbial growth to obtain one or more fermentation products are also provided herein. Such methods have the advantage of providing for both a valuable co-product in the extracted isoflavones as well as one or more fermentation products. Isoflavone-depleted soybean based medias provided herein can be used in place of current soybean-based fermentation medias are used to produce a wide variety of primary products that include, but are not limited to, a drug, a drug precursor, or a pesticide. Isoflavone-depleted soybean based medias provided herein can also be used in place of current soybean-based fermentation medias are used to produce a wide variety of other fermentation products that include, but are not limited to, a fermentation broth, an enzyme, a secondary metabolite, and/or a cultured microorganism.

Fermentation methods that use fermentation media comprising an isoflavone-depleted soybean meal or isoflavone-depleted soybean meal product can be used to obtain one or more fermentation products from any microorganism, that can be cultured on a soybean-based media. Microorganisms that can be cultured in fermentation media comprising an isoflavone-depleted soybean meal or isoflavone-depleted soybean meal product provided herein include, but are not limited to, an *Actinomycete*, a *Bacillus*, a *Staphylococcus*, or a fungus. Exemplary and non-limiting actinomycetes and fermentation products they produce that can be used in fermentation methods provided herein include, but are not limited to: i) *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus forma paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus forma glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine); ii) *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin); iii) *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis*, *S. fimbriatus*, *S. halstedii*, *S. rochei* and *S. viridochromogenes* (cephamycins A, B); *S. cattleya* (thienamycin); and *S. olivaceus, S. flavovirens, S. flavus, S. fulvoviridis, S. argenteolus*, and *S. sioyaensis* (MM 4550 and MM 13902); iv) *S. albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin); and v) *S. orientalis* and *S. haranomachiensis* (vancomycin); *S. candidus* (A-35512, avoparcin), and *S. eburosporeus* (LL-AM 374). The use of *Saccharopolyspora* species in general and *S. erythrea* (erythromycin) are specifically provided.

In certain embodiments, fermentation methods that use fermentation media comprising an isoflavone-depleted soybean meal or isoflavone-depleted soybean meal product and at least one exogenous added ingredient that comprises a substrate for microbial growth can provide a fermentation product yield equivalent to, or greater than, a fermentation product yield supported by a control fermentation medium comprising soybean meal or a soybean meal product and at least one exogenous added ingredient that comprises a substrate for microbial growth. Fermentation product yields can be determined in direct comparisons where a two fermentation processes that essentially differ only in the use of either a) an isoflavone-depleted soybean meal or isoflavone depleted soybean meal product; or b) a control soybean meal or soybean meal product that has not been subjected to an isoflavone extraction process. Thus, such controlled experiments would hold constant the microbial strain, the inoculum, temperature, pH, degree of aeration, degree of agitation, duration, and all other fermentation media components including, but not limited to, one or more substrates for microbial growth. Such controlled and parallel fermentation experiments can be used to determine if use of a fermentation media comprising an isoflavone-depleted soybean meal or isoflavone-depleted soybean meal product has an effect on fermentation product yield. However, those skilled in the art will recognize that even fermentation processes are subject to some variability in fermentation product yields. Consequently, such variability is expected to result in observed differences in fermentation product yield between fermentations performed isoflavone depleted soybean meal or isoflavone depleted soybean meal product and fermentations performed with control soybean meal or soybean meal product that in certain instances will not be statistically significant.

Nonetheless, fermentation media provided herein also include media where either the amount of isoflavone-depleted soybean meal or isoflavone-depleted soybean meal product and/or any other ingredients including, but not limited, to substrates for microbial growth, are independently varied relative to amounts used in control or conventional soybean based medias to provide for optimized fermentation product yields. In this regard, any fermentation parameter, including but not limited to, the microbial strain, the inoculum, temperature, pH, degree of aeration, degree of agitation, duration, and the like can also be varied relative to parameters used in control or conventional soybean based medias to provide for optimized fermentation product yields. Such optimization of media components and/or fermentation conditions that use fermentation media comprising an isoflavone-depleted soybean meal or isoflavone-depleted soybean meal can be achieved through empirical testing.

In certain embodiments, the soybean-based fermentation products provided herein through use of isoflavone-depleted soybean based fermentation medias comprise compositions that are distinct from the soybean-based fermentation products provided by use of conventional soybean-based fermentation medias. In particular, it is anticipated that qualitative and/or quantitative differences in the isoflavones and/or isoflavone biotransformation products produced can be attained by use of isoflavone-depleted soybean-based fermentation medias provided herein. Such isoflavone biotransformation products of soybean-based fermentations have been disclosed previously and can be measured (U.S. Pat. No. 5,554,519; U.S. patent application Ser. No. 11/464,700; Hessler et al., Appl. Microbiol Biotechnol, 47:398-404, 1997;

Chimura et al., J. Antibiot. 28, 619-626, 1975; Hosny and Rosazza, J. Nat. Prod. 62, 1609-1612, 1999; Komiyama, et al. J. Antibiotic 42, 1344-1349, 1989; Aoyagi, et al., J Antibiot (Tokyo), 28(12):1006-8; 1975; Hazato, et al., J. Antibiot. 32, 217-222, 1979; Maatooq and Rosazza, Phytochemistry 66(9):1007-11, 2005). Fermentation products produced by the methods provided herein that have reduced levels of isoflavones and/or isoflavone biotransformation products are thus provided.

A particular fermentation product of interest that can be produced by use of the isoflavone-depleted soybean based media provided herein is a spent fermentation beer. Such spent fermentation beer has been found to be useful as an animal feed additive. Exemplary and non-limiting examples of the use of spent fermentation beer as a feed additive are found in U.S. Pat. No. 6,616,953 and U.S. Pat. No. 6,090,416, each of which are incorporated herein by reference in their entireties. U.S. Pat. No. 6,616,953 describes compositions and methods for obtaining poultry feed additive from the spent fermentation beer obtained from fermentation of *Saccharopolyspora erythraea*. A process whereby the spent fermentation beer from *Saccharopolyspora erythraea*-mediated erythromycin production processes is first treated with acid and heat and then treated with a mixture of at least two enzymes is disclosed. The product of the acid, heat and enzyme treatments is then simply concentrated for use as poultry feed. It is thus anticipated that a spent fermentation beer obtained as a product of methods provided herein can be used to make a feed additive. Feed additives obtained from spent fermentation beer produced by the methods provided herein that have reduced levels of isoflavones and/or isoflavone biotransformation products are thus provided.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Strains and Growth Media

The erythromycin producing strain used for this study was the wild-type "white" *Saccharopolyspora erythraea* FL2267 a derivative of ATCC 11635 (American Type Culture Collection, Manassas, Va.). *S. erythraea* cultures were prepared in CFM1 broth (Carbohydrate-based Fermentation Medium. CFM1 per liter distilled water: Difco™ soluble starch, 60 g; Bcto™-soytone (Difco™), 20 g; $CaCl_2.2H_2O$ (Sigma), 0.1 g; Bacto™-yeast extract (Difco™), 1.5 g; MOPS, 26.5 g; pH adjusted to 6.8 with 4N NaOH (Sigma). Fermentations were performed in OFM1 broth (Oil-based Fermentation Medium). OFM1 contains insoluble medium components and is meant to closely correlate to an industrial-type fermentation medium. OFM1 per liter: toasted nutrisoy flour (ADM, Decatur, Ill.), 22 g; Difco™ soluble starch, 15 g; $CaCO_3$ powder (JT Baker, Phillipsburg, N.J.), 3 g; $MgSO_4.7H_2O$ (JT Baker, Phillipsburg, N.J.), 0.5 g; $FeSO_4.7H_2O$ (JT Baker, Phillipsburg, N.J.), 15 mg; Soy oil, 50 ml (ADM, Decatur, Ill.).

Example 2

Chemicals and Biochemicals

Genistein, daidzein, genistin, daidzin and robinin were purchased from Inofine Chemicals (Hillsborough, N.J.). The enzyme beta-glucosidase was purified from almonds (Sigma Aldrich Chemical Company, St. Louis, Mo.).

Example 3

Thin Layer Chromatographic Analysis

For analytical thin layer chromatographic ("TLC") experiments, Silica Gel 60 $F_{254}$ plates (Macherey-Nagel) with 0.2 mm thickness were used. The presence of a fluorescent indicator with a 254 nm excitation wavelength made possible identification of the isoflavone products that appeared as a dark spots at 306 nm (UVP transilluminator). Three solvent systems were used for identification of the isoflavones. First, chloroform:methanol:acetic acid (10:1:1) was found to be better for the separation of aglycones (genistein, daidzein) and, second, hexane:ethyl acetate:methanol (20:20:8) was used for the resolution of the glycosylated isoflavones ("spots A, B and C", genistin, daidzin). All reagents were HPLC grade. All samples for the TLC analyses were prepared as ethyl acetate solutions. As a standard 0.3 mg/ml ethyl acetate solutions of the pure isoflavones (Indofine, Hillsborough, N.J.) were used. The third general solvent system used was chloroform:MeOH:water (80:20:2).

Example 4

Stirred Jar Fermentation Method

The fermentation seed culture was prepared in 25 ml SCM (4× starch) shake flasks. Seven shake flasks were prepared per fermentor. The seed cultures were inoculated with 15 µl of 2-week old spores that had been stored in glycerol and frozen at −80° C. The flasks were incubated at 32° C. while shaking at 280 rpm with a 1-inch circular displacement and grown for 40 hours. The fermentation was performed in New Brunswick BioFlo 110 modular benchtop fermentors, using BioCommand Plus software Revision A 2002. The fermentors were filled with 2 L of sterile OFM1 broth and Inoculated with 100 ml of seed culture. One hundred milliliters of a 10% solution of sterile glucose was also added to the culture medium at this point. Crude soybean oil was added to the fermentation starting at 12 hour post inoculation at a rate of 3.3 ml/minute. Samples of the fermentation broth were taken at regularly scheduled intervals throughout the course of the 5-day fermentation, flash frozen in a −80° C. ethanol bath, and stored at −20° C. Fermentations were performed at 32.5° C., minimum agitation at 600 rpm, cascaded to maintain dissolved oxygen at above 20% for approximately 5-6 days. At the completion of the fermentation the cultures were streaked on E20A agar plates to check for contamination.

Example 5

Isoflavone-Depleted Fermentations: Isoflavone Aglycone Recovery

Soybean flour suspended in water was subjected to beta-glucosidase treatment prior to extraction with solvent. FIG. 1A shows the effects of isoflavone-depleted soybean flour on erythromycin production in five day shake flask fermentations using OFM1 medium. Yields of erythromycin fermentation product obtained with isoflavone-depleted soybean flour was equally as good, if not better, than yields of erythromycin fermentation product obtained in fermentations performed with natural (i.e. control) soybean flour that was not subject to isoflavone extraction (FIG. 1A). The average value for the control fermentation using untreated soybean flour was 970 ug/ml, whereas the ethyl acetate extracted soybean flour (lane 2) was 1096 ug/ml and the beta-glucosidase treated and ethyl acetate extracted soybean flour was 1084 ug/ml. Statistically, these differences fall within the margin of error of the measurements; nevertheless, the results showed that isoflavone-depleted soybean flour is an equivalent substitute for natural (i.e. control) soybean flour in the erythromycin fermentation.

TLC results (FIG. 1B) show that the enzyme treatment resulted in the production of isoflavone aglycones seen as the appearance of dark bands for genistein and daidzein (G and D, lane 6) compared to the relative lack of these compounds in the untreated soybean flour (FIG. 1B, lane 5). Furthermore, the aglycones were efficiently extracted from the soybean flour with ethyl acetate. Erythromycin fermentations were performed using the isoflavone-depleted soybean flour generated in this experiment.

Example 6

Isoflavone-Depleted Fermentations: Isoflavone Glucoside Recovery

Experiments were conducted to determine whether soybean flour could be extracted in dry form rather than in an aqueous suspension. The experiments also addressed the type of solvent that would be best for performing a dry extraction of the soybean flour, comparing four different solvents. Solvent extraction of dry soybean flour was performed without suspension of the soybean flour in water and without beta-glucosidase treatment. This approach led to the recovery of primarily isoflavone glucosides, genistin and daidzin, as opposed to isoflavone aglycones, since the isoflavone glucosides are the predominant isoflavone species in untreated soybean flour.

Three different solvents were used to extract soybean flour prior to using the soybean flour as an erythromycin fermentation medium component: i) ethyl acetate ii) 95% ethanol-water; and iii) 50% ethanol-water (FIG. 2, Panel A, erythromycin production: Lane 1, control soybean flour, no extraction; lane 2, isoflavone-depleted soybean flour, ethyl acetate extraction; lane 3, isoflavone-depleted soybean flour, 95% ethanol extraction; and lane 4, isoflavone-depleted soybean flour, 50% aqueous ethanol extraction). Extraction of soybean flour was performed with: lane 5, ethyl acetate; lane 6, 95% ethanol; lane 7, methanol; and lane 8, n-propanol and analyzed by TLC (FIG. 2, Panel B). The treated soybean flours were compared in shake flask fermentations for their effects on erythromycin yield. All four soybean flours behaved similarly with the ethyl acetate extracted soybean flour showing a slight increase in production over the control and ethanol extracted soybean flours. The soybean flours were subjected to an overnight extraction period without mixing.

Although the extraction of soybean flour with ethyl acetate gave the best erythromycin yields of the solvents tested (FIG. 2A), the ethyl acetate also showed the weakest recovery of isoflavone glucosides of any solvent tested (FIG. 2B). This is probably because ethyl acetate was the least polar of the solvents tested. All four solvents separated well from the soybean flour. However, the methanol extract turned a yellow color and was cloudy, indicating extraction with methanol removed more non-isoflavone material than the other solvents. The 95% ethanol extract also showed good recovery of isoflavone glucosides without the co-extraction of pigmented compounds that was seen with methanol. The 95% ethanol extracted soybean flour also performed as well as natural (i.e. control) flour in erythromycin fermentations. S, reference standards.

Example 7

Stirred Ethanol Extraction Method

The use of fermentation media comprised of isoflavone-depleted soybean flour produced with a 95% ethanol/water had no negative impact on the erythromycin fermentation product yield, and the recovery of isoflavones from this solvent was relatively good. A 95% ethanol/water solvent was mixed with soybean flour for 2 or 12 hours, rather than simply steeped in the solvent (as in Example 6). The solvent was separated from the soybean flour by settling or centrifugation. The extracted soybean flour was then used in a standard erythromycin shake flask fermentation, using eight flasks per class. The resulting extracted soybean flour was used in the fermentation medium even though it was still wetted with the solvent. S. erythraea strain FL2267 was used in this experiment. Fermentation medium was OFM1+ oil. The results (FIG. 3A) show that the stirred extraction method does not destroy the isoflavone-depleted soybean flour's usefulness for the erythromycin fermentation. Surprisingly, the results show that the extracted soybean flour that is isoflavone depleted performs equally as well, if not better than the untreated soybean flour that is not isoflavone depleted. Lane C, no soybean flour treatment; lane 1, 2 hour extraction with 95% ethanol; lane 2, 12 hour extraction with 95% ethanol.

The recovered solvent was concentrated and analyzed by thin layer chromatography. FIG. 3B shows the solvent contains isoflavone glucosides. The longer extraction time (12 h) gave a slightly more intense spot on TLC for genistin and daidzin, indicating that longer extraction time improved the recovery of the isoflavone glucosides without having a negative effect on erythromycin yield. Lane S, isoflavone reference standards; lane 1, 2 hour extraction with 95% ethanol; lane 2, 12 hour extraction with 95% ethanol.

FIG. 3C shows the results of stirred extraction of soybean flour with 50% ethanol. Extraction with 50% ethanol while mixing may improve isoflavone glucoside recovery (compare intensity of g and d spots in FIGS. 3C and D). However, it also had a significant negative effect on erythromycin yield making this recovery method less desirable in certain applications where higher erythromycin yields are required. FIG. 3C: Lane C, erythromycin production, control soybean flour, no treatment; lane 3, 2 hour extraction with 50% ethanol; lane 4, 12 hour extraction with 50% ethanol; FIG. 3D, TLC analysis: Lane S, isoflavone reference standards; lane 1, 2 hour extraction with 50% ethanol; lane 2, 12 hour extraction with 50% ethanol.

Example 8

The Effects of Ethanol Concentration on Isoflavone Recovery and Antibiotic Production The effect of five different ethanol concentration on isoflavone recovery and erythromycin yield in a soybean-based fermentation was determined.

FL2267, a wild type, white strain of S. erythraea was grown in OFM1 containing soybean flour that was either: i) extracted with 95%, 90%, 85%, 80%, or 75% ethanol; or ii) not extracted (unextracted control). Fermentations were performed essentially as described in Example 1 using 250-ml shake flasks and shaken at 380 rpm at 32° C. Fermentations were carried out for five days to obtain the data reported in FIG. 4. For HPLC analysis (FIG. 5 5) a Prevail C18 column was used (5 micron, 250 mm×4.6 mm column), 30° C., with UV detection at 260 nm.

Figure 5:
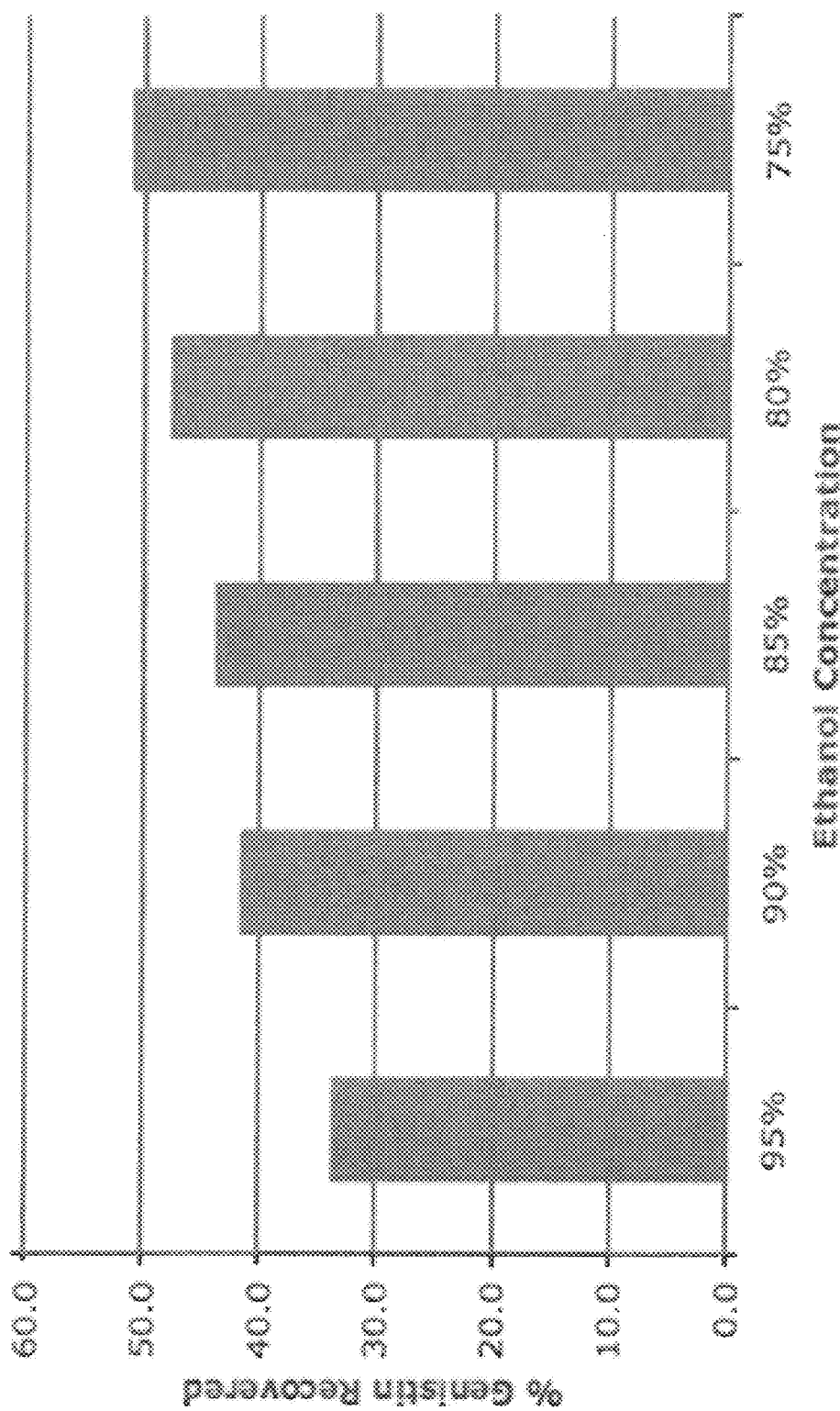
FIG. 5 shows the effect of ethanol concentration on the efficiency of extraction of isoflavones from soy flour.

Ethanol extraction with 95% ethanol showed a statistically significant improvement in erythromycin production by 30% relative to the cultures grown on control broth containing unextracted soybean flour. At the lower ethanol concentrations of 90%, 85% and 80%, the benefit to erythromycin production was lower (FIG. 4), but the isoflavone recovery was increased (FIG. 5). At 75% ethanol, the extraction process begins to show a negative effect on erythromycin production. This is consistent with what had been seen earlier, when even lower concentrations of ethanol (50%) were found to have even more severe negative effects on production (FIG. 3C).

The ethanol extraction procedure on soybean flour using 95% ethanol has a significant positive effect on erythromycin production of approximately 30%. Isoflavone recovery using 95% ethanol, however, is about 15% lower than the best method tested, which was using 75% ethanol extraction. The decision of what ethanol concentration to use on soybean flour will depend on the relative value of the erythromycin versus the isoflavones that are recovered. Currently, the added value of the 30% erythromycin increase is more significant than the added value of the additional isoflavones that could be recovered at 75% ethanol, therefore the best procedure based on the current data would be to perform the ethanol extractions at 95% ethanol.

Subsequently, experiments were performed to determine the reason for the increase in erythromycin production. In one experiment the soybean flour, which had been wetted with 95% ethanol during the extraction process, was dried by evaporation to a powder. The extracted and dried soybean flour was then compared to unextracted dry soybean flour in the erythromycin fermentation and it was found that the performance of the dried soybean flour was indistinguishable from the unextracted dried soybean flour. This experiment indicated that the presence of ethanol in the fermentation media provided for at least some of the observed increases in erythromycin production.

A second experiment was performed in which 95% ethanol was added directly to the fermentation medium containing unextracted soybean flour at a concentration range of 1-7%. It was found that ethanol at a final concentration of 1% gave a 20% boost in erythromycin production, that 2% ethanol gave a 6% boost, and all other levels of ethanol greater than 2% caused significant decreases in erythromycin production. Without seeking to be limited by theory, it may be that saturating soybean flour with ethanol, as is done during the isoflavone recovery process, is a more effective way to deliver ethanol to the erythromycin fermentation since it results in the higher boost in production than is seen when the ethanol extraction process is used. Addition of ethanol directly to the fermentation broth can also provide for increased antibiotic yields, but has a narrow concentration range that is effective. The data indicates thus that a significant portion of the observed increase in erythromycin production when using ethanol extracted soyflour is likely due to the ethanol in the medium, and not due to the removal of the isoflavones. However, the very best yields of erythromycin (30%) were obtained in these experiments when using soybean flour extracted with 95% ethanol, so it is possible that there is an additive and/or synergistic effect provided by combining the ethanol and the extracted soybean flour.

In summary, the best erythromycin production in these experiments was obtained when 95% ethanol was used to extract the soybean flour. The use of 95% ethanol in the soybean flour extraction produced the greatest increase in erythromycin production (30%), with an acceptable level of isoflavone recovery. The best isoflavone recovery was obtained in these experiments when 75% ethanol was used to obtain the extracted soybean flour.

Example 9

Measuring Isoflavone Recovery and Purity Levels Using the 95% Ethanol Extraction Method In Example 8, the recovery and purity levels of recovered isoflavones were only roughly estimated based on intensity of spots on TLC plates. In this experiment, the isoflavone recovery and purity were measured more precisely using HPLC (FIGS. 6 A &B) and dry weight determinations on the recovered pure product.

The extraction and analysis were performed as follows.
1. Transferred 22 g of soybean flour into six 250-ml centrifuge bottles (132 g of soybean flour total).
2. Added 130 ml of 95% ethanol to each bottle (780 ml total).
3. Mixed bottle contents on an orbital shaker at 300 rpm and 65° C. for 2 hrs.
4. Centrifuged bottles at 10K for 1 min, alternatively, let soybean flour settle out.
5. Collected 660 ml of ethanol extract into a beaker (120 ml of ethanol remains behind in the soybean flour).
6. Evaporated the ethanol extact until no ethanol remains, leaving about 12 ml of viscous liquid.
7. Transferred concentrated extract to a 50 ml corning tube.
8. Added 24 ml distilled water and 0.5 g beta-glucanase to the concentrated extract, incubate at 45° C. overnight.
9. Distributed the digested concentrated extract between two 50 ml tubes with 18 ml in each tube.
10. Added 20 ml of EtOAc to each tube, mix well.
11. The tube contents were separated into two layers upon standing, or can be separated more quickly by centrifuging for 10 min at 4K.
12. Transferred the top solvent layer of both tubes (36 ml total) to a round bottom flask and evaporate at 60° C. until all the Ethyl Acetate is removed.
13. About 2 ml of liquid was obtained that contained a precipitate (ppt).
14. Transferred the liquid with the ppt into a new 15 ml tube.
15. Recovered ppt by centrifugation of the liquid.
16. Decanted the supernatant from the tube containing the 1st ppt.
17. Added 6 ml of water to the supernatant, then added 200 ul of glacial acetic acid. 18. A second precipitate formed.
19. Centrifuged and collected the pellets. Discarded the supernatants and retained the pellets as precipitate 2.

Figure 6A:
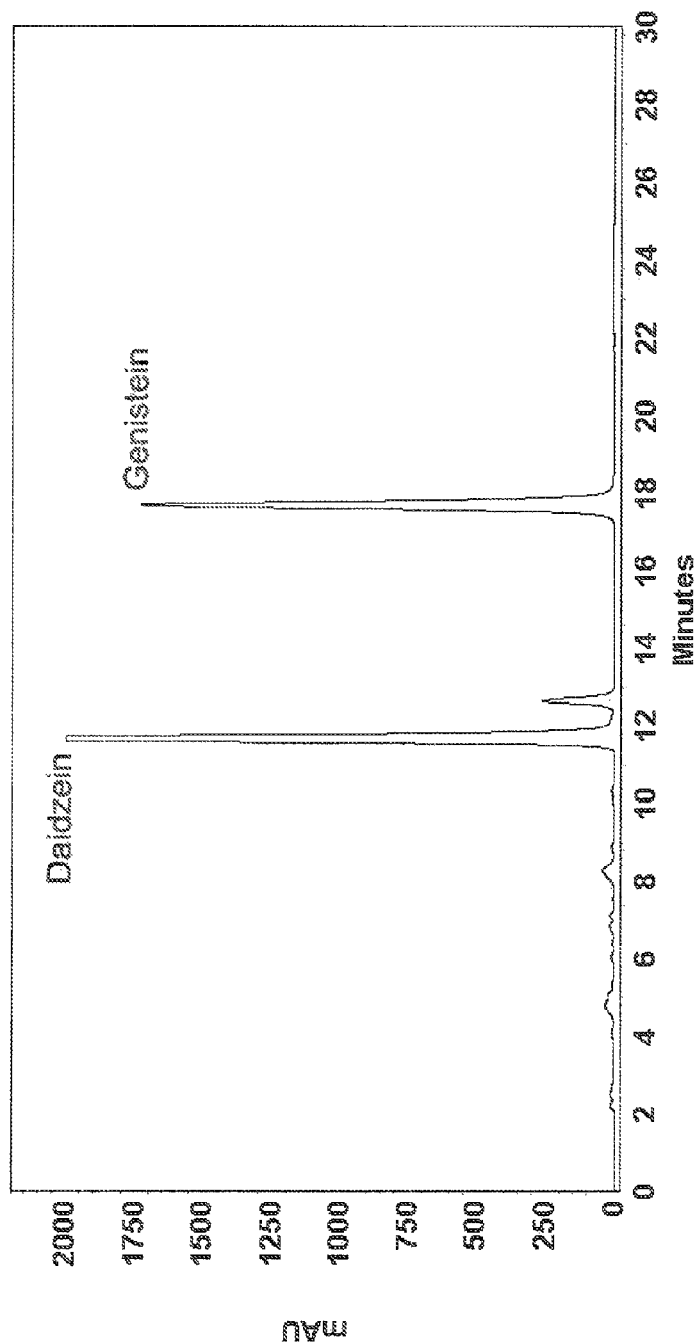
FIGS. 6A, B & C show HPLC results on recovery and purity of isoflavones from the soyflour using a 95% ethanol extraction methods. A. First precipitate. B. Second precipitate. C. Recovery and purity of the isoflavones recovered in precipitates 1 and 2, using the ethanol extraction protocol.
Figure 6B:
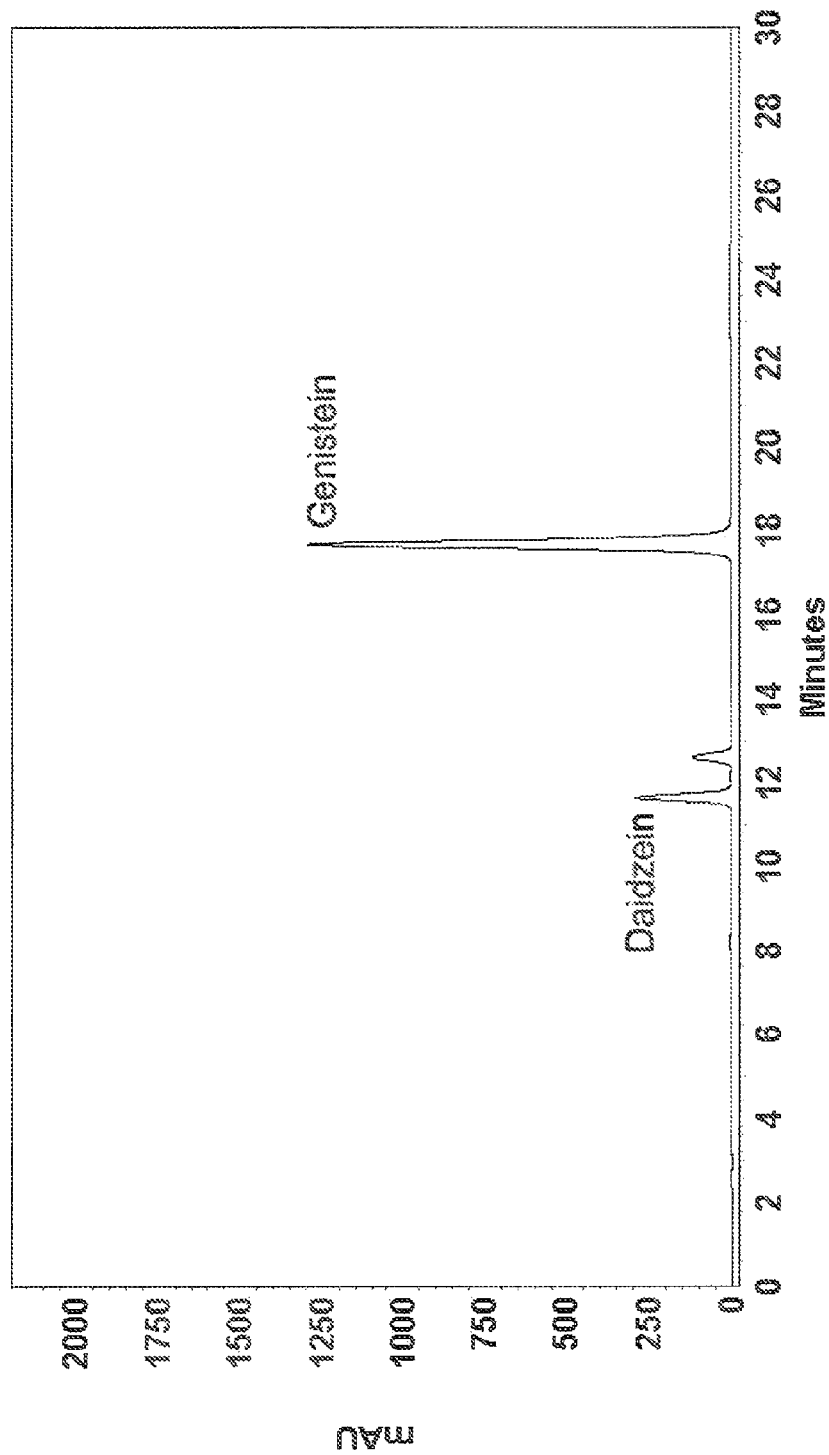

Results. The HPLC results of a representative experiment are shown (FIGS. 6A and B). The final coproduct is recovered in two separate precipitations whose recovery and purity were measured separately (FIG. 6C). The recovery percentage is based on the expected values for isoflavone content in soybean flour (based on USDA-Iowa State University Database on the Isoflavone Content of Foods—1999).

The protocol for the recovery of isoflavones with the 95% ethanol extraction method resulted in the recovery of isoflavones at about 25% of the theoretical maximal level possible, and at a purity of 43%. Recovery can potentially be improved by modifications in the recovery process. Methods for improving recovery include, but are not limited to, any of: i) performing two or more extractions of the soybean flour; and/or ii) increasing the time of extraction; and/or iii) increasing the temperature of extraction (i.e. from ambient or about 25° C. to a range of about 26° C. to 30° C., 26° C. to 40° C., 26° C. to 50° C., or 26° C. to 60° C.); and/or iv) increased mixing duration; and/or v) increased degree of mixing; and/or vi) performing additional precipitations of the isoflavones from the concentrated extract; and/or vii) reducing the temperature of the precipitation step; or any combination of i-vii. The purity of the isoflavone products is sufficient for use in most nutraceutical applications.

Example 10

Additional Results with the Ethylacetate Extraction Method

Background. Ethyl acetate extraction can also be used to remove isoflavones from soybean flour. In certain embodiments, the extraction is performed on aqueous suspension of enzyme-digested soybean flour, rather than on dry soybean flour as in the ethanol extraction method (above). The process of ethyl acetate extraction removes the isoflavone coproduct from the soybean flour, and it improves the efficiency of the erythromycin fermentation. The results of the ethyl acetate extraction process are reported previously. In FIG. 1, the ethyl acetate extraction process was performed on enzyme-digested and non-digested soybean flour, with both soybean flour treatments resulting in a 13% improvement in the efficiency of the erythromycin fermentation. In the experiment shown in FIG. 2 a 22% increase in erythromycin production was observed. In the experiment reported here, the effect of ethyl acetate extraction on isoflavone recovery and erythromycin production using a larger number of fermentations over a range of different enzyme treatment temperatures was examined.

Methods. The microbial strain used was FL2267, a wild type, white strain of *S. erythraea*. The medium used was OFM1 with soybean flour that was extracted with ethyl acetate. Both the soybean flour and the layer of water that the soybean flour was suspended in for the enzyme (Beta-Glucanase, Bio-Cat, Inc. Troy, Va., US) digestion and solvent extraction, were retained for use in the erythromycin fermenation. Fermentations were performed as usual in 250-ml shake flasks and shaken at 380 rpm at 32° C. Fermentations were carried out for five days to obtain the date shown in FIG. 4. For HPLC analysis (FIG. 5) a Prevail C18 column was used (5 micron, 250 mm×4.6 mm column), 30° C., using UV detection at 260 nm.

Figure 7:
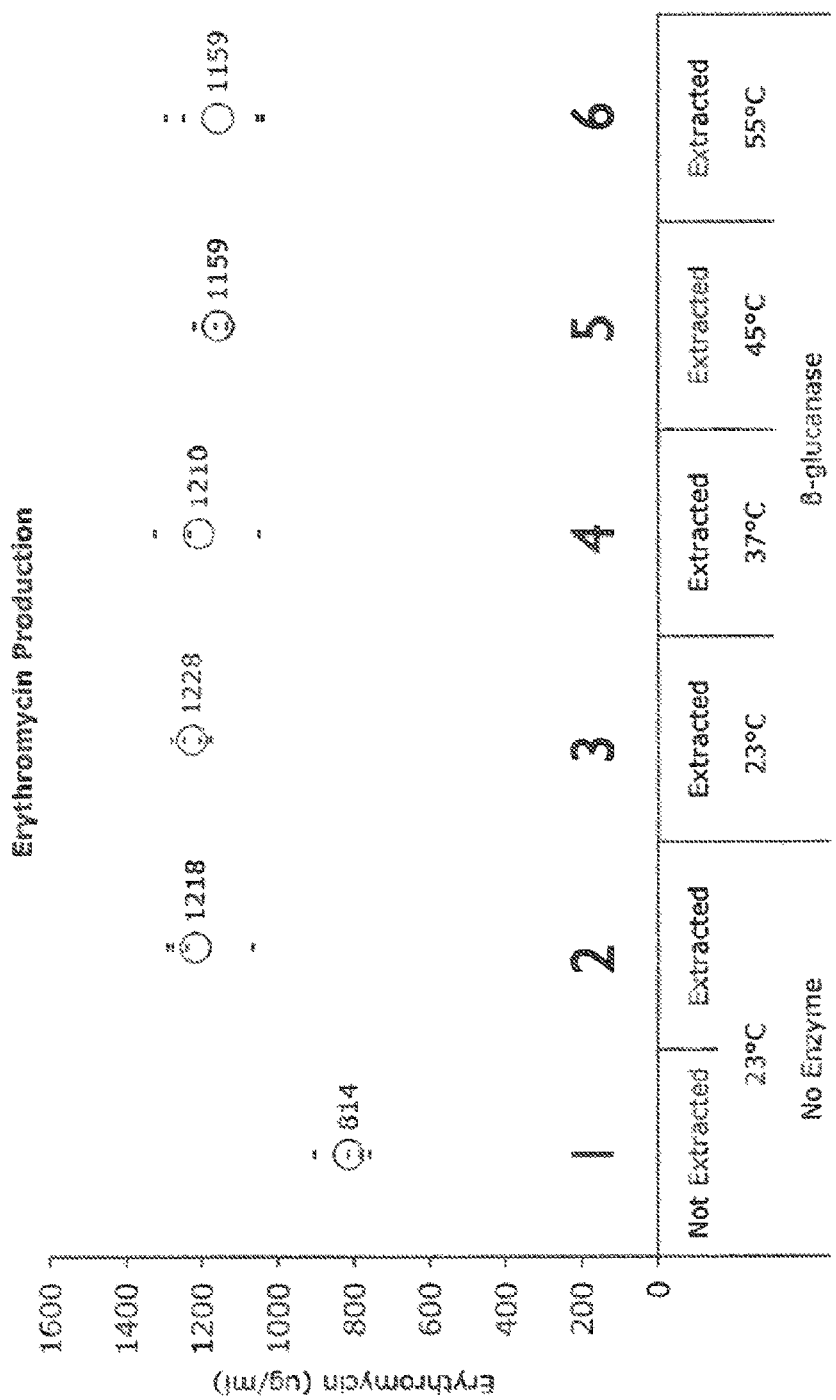
FIG. 7. Shows the effects of the extraction of isoflavones by ethyl acetate on erythromycin production. Six different samples were analyzed. Lane 1, Not extracted, 23° C. is the control sample; lane 2, extracted with ethyl acetate without being previously digested with beta glucanase; lanes 3-6, all were enzyme digested prior to ethyl acetate extraction at the temperatures shown.

The ethyl acetate extraction process that was performed on enzyme digested soybean flour resulted in a statistically significant improvement in erythromycin production by 40-50%. The results also show that the temperature at which the enzyme digestion is performed does not have a strong influence on the outcome of the fermentation (FIG. 7). The strain improvement effect was obtained regardless of whether the soybean flour was subjected to an enzyme treatment process.

Some of the advantages of the ethyl acetate extraction method over the ethanol extraction method are that the ethyl acetate extraction method requires only one solvent extraction step, whereas the ethanol extraction method requires both an ethanol extraction and an ethyl acetate extraction. Also, a higher recovery level is achieved and a higher purity product can be made using the ethyl acetate recovery method. Subsequent experiments were performed which showed that after the soybean flour is treated with beta-glucanase, and then extracted with ethyl acetate, the fermentation must be performed using both the treated soybean flour and the extracted aqueous layer in order to achieve the boost in erythromycin production. If the aqueous layer is not used in the subsequent fermentation, then the efficiency of erythromycin production drops 30% or more.

Subsequently, experiments were performed to determine the reason for the increase in erythromycin production. In one experiment the soybean flour, which had been wetted, enzyme digested, and then extracted with ethyl acetate, was dried by evaporation to a powder. The extracted and dried soybean flour was then compared to unextracted dry soybean flour in the erythromycin fermentation and it was found that the performance of the treated soybean flour was approximately 30% lower than the unextracted dried soybean flour. This experiment pointed to the aqueous layer as containing some necessary agent for optimal erythromycin production.

A second experiment was performed in which ethyl acetate was added directly to the fermentation medium at a concentration range of 2, 4, and 6%. It was found that ethyl acetate at a concentration of 6% gave a 30% boost in erythromycin production, that 4% ethyl acetate gave a 20% boost, and 2% gave a 6% boost. Again, it may be that saturating soybean flour with ethyl acetate, as is done during the isoflavone recovery process, is a more effective way to deliver ethyl acetate to the erythromycin fermentation since it results in the higher boost in production than is seen when ethyl acetate is simply directly added to the fermentation broth. The data indicates that a significant portion of the observed increase in erythromycin production using soybean flour extracted by an ethyl acetate procedure is due to the ethyl acetate in the medium, and not due to the removal of the isoflavones. However, the very best yields of erythromycin (40%-50%) were obtained in these experiments when using enzyme digested soybean flour that was extracted with ethyl acetate, so it is possible that there is an additive and/or synergistic effect provided by combining the ethyl acetate and the extracted soybean flour.

Example 11

Measuring Isoflavone Recovery and Purity Levels Using the Ethyl Acetate Extraction Method In this experiment, the isoflavone recovery and purity were measured for the ethyl acetate recovery process using HPLC (FIG. 8) and dry weight determinations on the recovered pure product.

Method used to extract isoflavones from soybean flour using ethyl acetate
1. Measured out 22 g soybean flour in a bottle.
2. Add 100 mL dH2O and 0.5 g β-glucanase into the tube.
3. Incubate at 45° C. overnight.
4. Add 130 mL of ethyl acetate and mix.
5. Separate the solvent from the aqueous layer and transfer it to a 125 mL round bottom flask.
6. Keep the soybean flour, and the water layer and the interface layer between the two liquid layers, and used in the erythromycin fermentation medium.
7. Evaporate the EtOAc (from step 6) down to 1 mL and transfer the 1 ml volume a 15 mL conical tube.
8. Add 1 mL of EtOAc to the round bottom flask to get the left over precipitate out and add to the same 15 mL tube.

9. Let the tube sit open at room temperature overnight to form a precipitate.
10. Spin down the tube and collect the first precipitate as the first part of the final product.
11. Transfer the supernatant to another tube.
12. Treat the supernatant with 500 uL of 10% Glacial Acetic Acid and vortex.
13. Evaporate the EtOAc out of the water and spin everything down in an Eppendorf tube, collect the precipitate as the second part of the final product.
14. The supernatant can be discarded.

Performance of HPLC and Dry Weight determinations.
1. Resuspended the two pellets with 1 mL EtOAc.
2. Used 100 uL to do a dry weight analysis.
3. Used 1:50 dilution to inject 10 uL into HPLC.

Figure 8A:
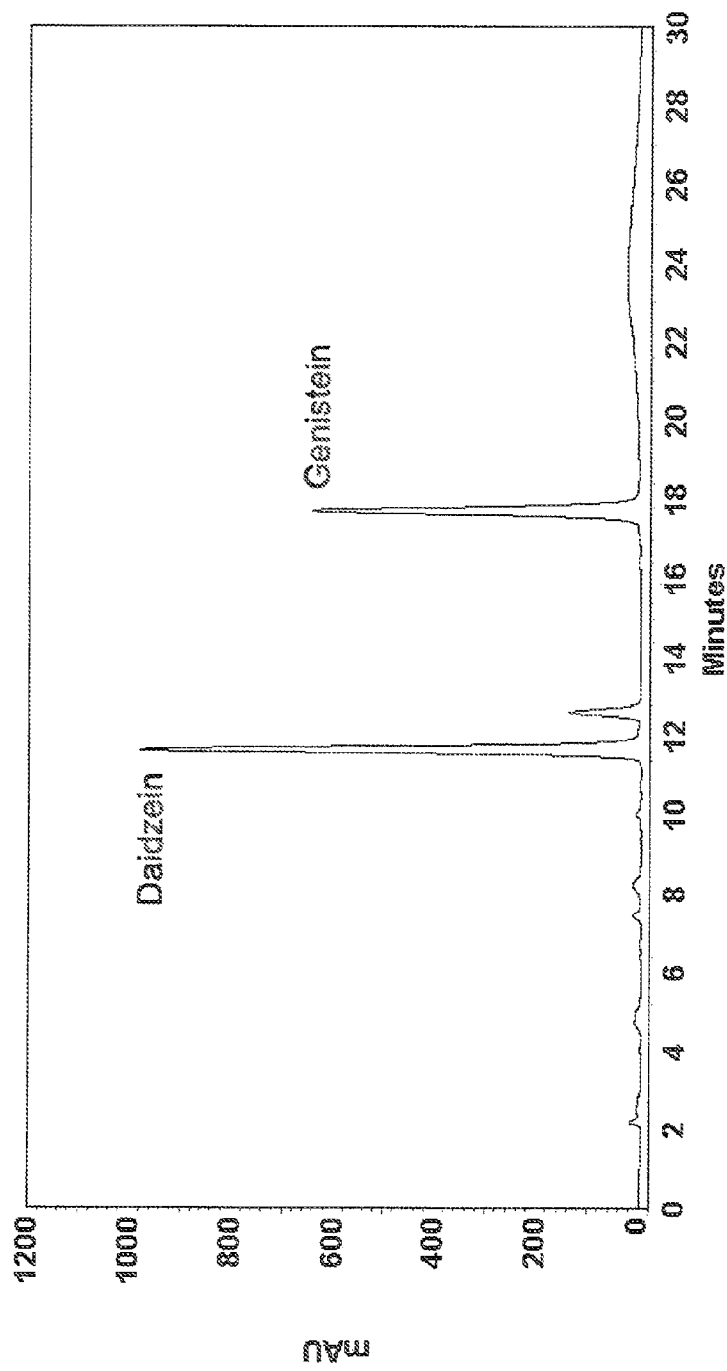
FIGS. 8. A, B, and C show an HPLC analysis of the isoflavones obtained using an ethyl acetate recovery process. A. HPLC analysis of the first precipitate. B. HPLC analysis of the second precipitate. C. Recovery and purity of the isoflavone products recovered from the ethyl acetate extraction method.
Figure 8B:
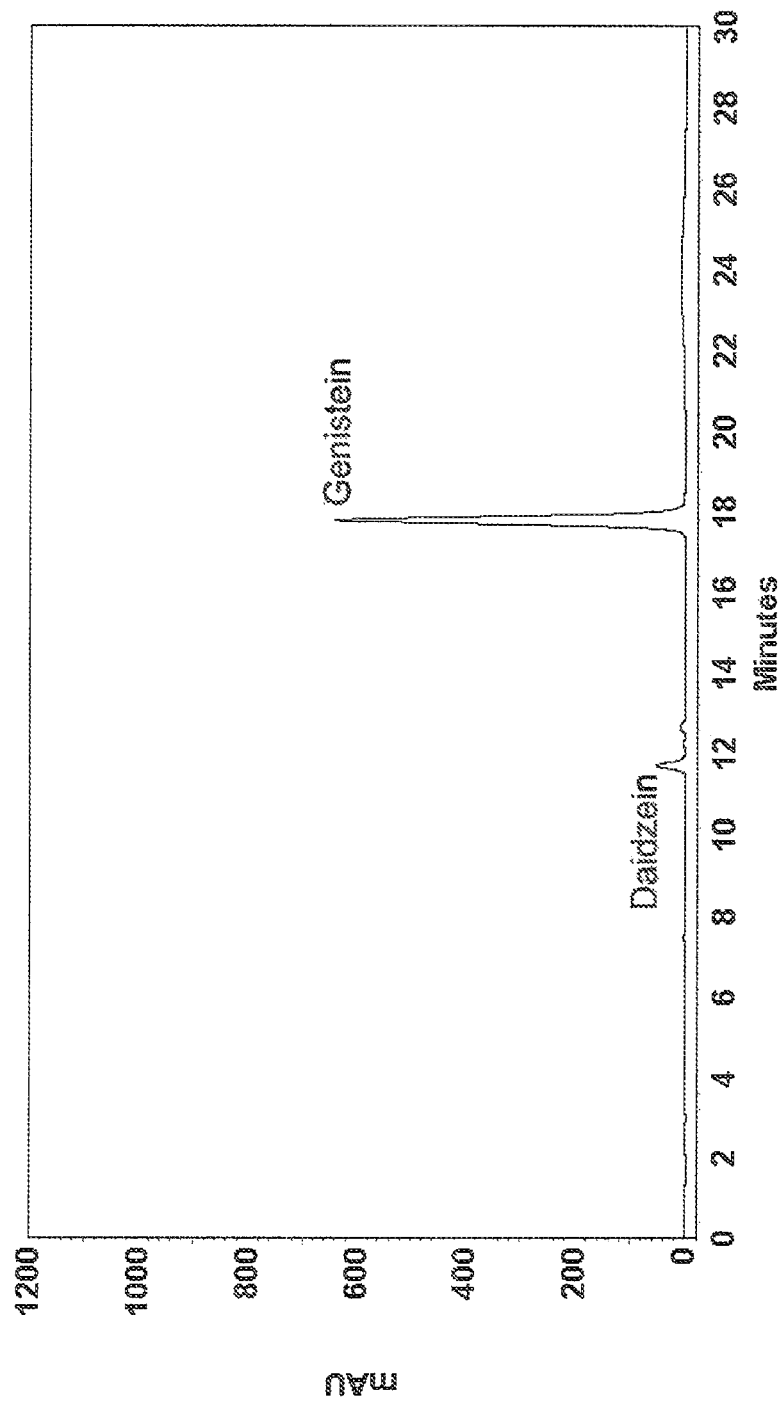

The HPLC results of a representative experiment are shown (FIGS. 8A and B). The final co-product is recovered in two separate precipitations whose recovery and purity were measured separately (FIG. 8C). The recovery percentage is based on the expected values for isoflavone content in soybean flour (based on USDA-Iowa State University Database on the Isoflavone Content of Foods—1999).

This protocol for the recovery of isoflavones with the ethyl acetate extraction method to resulted in the recovery of isoflavones at 48% of the theoretical maximal level possible, and at a purity of 80%. The levels of recovery can potentially be improved by modifications in the recovery process. Methods for improving recovery of isoflavones include, but are not limited to, any of: i) performing two or more extractions of the soybean flour; and/or ii) increasing the time of extraction; and/or iii) increasing the temperature of extraction (i.e. from ambient or about 25° C. to a range of about 26° C. to 30° C., 26° C. to 40° C., 26° C. to 50° C., or 26° C. to 60° C.); and/or iv) increased mixing duration; and/or v) increased degree of mixing; and/or vi) performing additional precipitations of the isoflavones from the concentrated extract; and/or vii) reducing the temperature of the precipitation step; and/or vii) increasing time and/or the specific activity of beta-glucanase used; or any combination of i-viii. The purity of the isoflavone products obtained herein is sufficient for use in nutraceutical applications. Compared to the ethanol extraction method of Example 8, the ethyl acetate extraction method disclosed in this Example results in a greater isoflavone recovery and a higher purity product.

In view of the above, it will be seen that the several advantages of the invention are achieved and other advantageous results attained. As various changes could be made in the above methods and compositions without departing from the scope of the invention, it is intended that all matter contained in the above description and shown in the accompanying drawings shall be interpreted as illustrative and not limiting in a limiting sense. Thus, the breadth and scope of the present invention should not be limited by any of the above-described exemplary embodiments, but should be defined only in accordance with the following claims appended hereto and their equivalents.

What is claimed is:

1. A method of obtaining at least one fermentation product, said method comprising the steps of:
    a. culturing a microorganism in a fermentation medium comprising an isoflavone-depleted soybean meal or isoflavone-depleted soybean meal product and at least one exogenous added ingredient that comprises a substrate for microbial growth; and
    b. isolating a fermentation product from a culture wherein said culture comprises a fermentation broth and said microorganism from step (a), thereby obtaining at least one fermentation product.

2. The method of claim 1, wherein said isoflavone-depleted soybean meal or isoflavone-depleted soybean meal product is obtained by treating soybean meal or a soybean meal product with at least one agent that converts an isoflavone glucoside to an isoflavone and extracting said treated soybean meal or soybean meal product with a solvent.

3. The method of claim 1, wherein said isoflavone-depleted soybean meal or isoflavone-depleted soybean meal product is obtained by extracting soybean meal or a soybean meal product with a solvent.

4. The method of claim 1, wherein said method provides a fermentation product yield equivalent to, or greater than, a fermentation product yield supported by a control fermentation medium comprising soybean meal or a soybean meal product and at least one exogenous added ingredient that comprises a substrate for microbial growth.

5. The method of claim 4, wherein said fermentation media further comprises ethanol or ethyl acetate.

6. The method of claim 5, wherein ethanol is at a concentration of about 1% to about 2% by volume in said fermentation media.

7. The method of claim 5, wherein said ethyl acetate at a concentration of about 2% to about 6% by volume in said fermentation media.

8. The method of claim 1, wherein said microorganism is an *Actinomycete*, a *Bacillus*, a *Staphylococcus*, or a fungus.

9. The method of claim 8, wherein said actinomycete is selected from the group consisting of *Streptomyces, Streptosporangium, Actinoplanes, Micromonospora, Geodermatophilus, Nocardioides, Saccharothrix, Amycolatopsis, Kutzneria, Saccharomonospora, Saccharopolyspora, Kitasatospora, Microbispora, Actinomadura,* and *Saccharopolyspora*.

10. The method of claim 9, wherein said actinomycete is selected from the group consisting of *Streptomyces rimosus, Streptomyces fradiae, Streptomyces hygroscopicus, Streptomyces cinnamonensis, Streptomyces peucetius, Saccharopolyspora erythraea, Streptomyces avermitilis, Streptomyces glaucescens, Streptomyces violaceoniger, Streptomyces kanamyceticus, Streptomyces clavuligerus,* and *Streptomyces roseolous*.

11. The method of claim 10, wherein said actinomycete is *Saccharopolyspora erythraea*.

12. The method of claim 1, wherein at least one of said fermentation products is a drug, a drug precursor, or a pesticide.

13. The method of claim 12, wherein said drug is an antibiotic, an animal growth modulator, an anti-cancer agent, an immunosuppressant, an anti-hypertensive agent, or an anti-parasitic agent and wherein said pesticide is an insecticide.

14. The method of claim 12, wherein said drug or a drug precursor is selected from the group consisting of oleandomycin, actinomycin, avermectin, lasalocid, tetracenomycin, tetracycline, oxytetracycline, tylosin, rapamycin, daunorubicin, rifamycin, monensin, and erythromycin.

15. The method of claim 14, wherein said drug or drug precursor is erythromycin and said actinomycete is *Saccharopolyspora erythraea*.

16. The method of claim 1, wherein said fermentation medium comprising an isoflavone-depleted soybean meal or isoflavone-depleted soybean meal product has a total isoflavone aglycone content of less than about 125 milligrams total isoflavone aglycones per liter.

* * * * *